United States Patent
Pollen et al.

(10) Patent No.: US 10,016,547 B2
(45) Date of Patent: Jul. 10, 2018

(54) FOOLPROOF VALVE ASSEMBLY FOR A BREAST MILK COLLECTOR

(71) Applicants: Ashia M. Pollen, Madison, WI (US); Robert J. Harter, La Crosse, WI (US)

(72) Inventors: Ashia M. Pollen, Madison, WI (US); Robert J. Harter, La Crosse, WI (US)

( * ) Notice: Subject to any disclaimer, the term of this patent is extended or adjusted under 35 U.S.C. 154(b) by 564 days.

(21) Appl. No.: 14/685,649

(22) Filed: Apr. 14, 2015

(65) Prior Publication Data

US 2015/0217033 A1 Aug. 6, 2015

(51) Int. Cl.
*A61M 1/06* (2006.01)
*A61M 1/00* (2006.01)

(52) U.S. Cl.
CPC ............ *A61M 1/06* (2013.01); *A61M 1/0049* (2013.01); *A61M 1/062* (2014.02); *A61M 1/064* (2014.02)

(58) Field of Classification Search
CPC ......... A61M 1/06; A61M 1/062; A61M 1/064
See application file for complete search history.

(56) References Cited

U.S. PATENT DOCUMENTS

| 155,720 A | 10/1874 | Gray |
|---|---|---|
| 684,078 A | 10/1901 | Martin |
| 3,840,012 A | 10/1974 | Rushton, Jr. |
| 4,263,912 A | 4/1981 | Adams |
| 4,270,538 A | 6/1981 | Murphy |
| 4,425,935 A | 1/1984 | Gonzalez |
| 4,582,073 A | 4/1986 | Simkanich |
| 4,673,388 A | 6/1987 | Schlensog et al. |
| 4,857,051 A | 8/1989 | Larsson |
| 4,892,517 A | 1/1990 | Yuan et al. |
| 4,929,229 A | 5/1990 | Larsson |
| 5,009,638 A | 4/1991 | Riedweg et al. |
| 5,071,403 A | 12/1991 | Larsson |
| 5,295,957 A | 3/1994 | Aida et al. |
| 5,358,476 A | 10/1994 | Wilson |
| 5,571,084 A | 11/1996 | Palmer |
| 5,720,722 A | 2/1998 | Lockridge |
| 5,941,847 A | 8/1999 | Huber et al. |
| 5,954,690 A | 9/1999 | Larsson |
| 6,004,186 A | 12/1999 | Penny |
| 6,379,327 B2 | 4/2002 | Lundy |
| 6,440,100 B1 | 8/2002 | Prentiss |
| 6,575,202 B2 | 6/2003 | Lafond |
| 6,652,484 B1 | 11/2003 | Hunckler et al. |
| 6,706,012 B2 | 3/2004 | McKendry et al. |
| 6,764,377 B2 | 7/2004 | Gillan |
| 6,821,185 B1 | 11/2004 | Francis |
| 6,866,558 B2 | 3/2005 | Luciano et al. |
| 6,887,217 B1 | 5/2005 | Logan |
| 6,974,361 B2 | 12/2005 | Cravaack et al. |

(Continued)

*Primary Examiner* — Nathan R Price
*Assistant Examiner* — Melissa A Snyder
(74) *Attorney, Agent, or Firm* — bobharter.com; Robert J. Harter

(57) ABSTRACT

A breast pump system includes a duckbill-style check valve that intermittently releases breast milk from a charging chamber to a storage chamber. Various examples of rotational interlocks ensure that the valve is properly installed to avoid interference between the valve's discharge end and the inner surface of an outer shell that contains the valve. In some examples, the outer shell includes a concavity or other feature configured to accommodate multiple rotational positions of the valve.

20 Claims, 24 Drawing Sheets

(56) References Cited

U.S. PATENT DOCUMENTS

| | | | |
|---|---|---|---|
| 7,094,217 B2 | 8/2006 | Fialkoff | |
| 7,128,877 B2 | 10/2006 | Quay et al. | |
| 7,223,255 B2 | 5/2007 | Myers et al. | |
| 7,559,915 B2 | 7/2009 | Dao et al. | |
| 8,075,516 B2 | 12/2011 | Pfenniger et al. | |
| 8,118,772 B2 | 2/2012 | Dao et al. | |
| 8,414,353 B1 | 4/2013 | Leavell | |
| 8,529,501 B2 | 9/2013 | Wach et al. | |
| 8,568,350 B2 | 10/2013 | Schlienger et al. | |
| 8,702,646 B2 | 4/2014 | Garbez et al. | |
| 8,801,495 B1 | 8/2014 | Guindon | |
| 2014/0052056 A1* | 2/2014 | Garbez | A61M 1/062 604/74 |

* cited by examiner

FIG. 7
FIG. 8
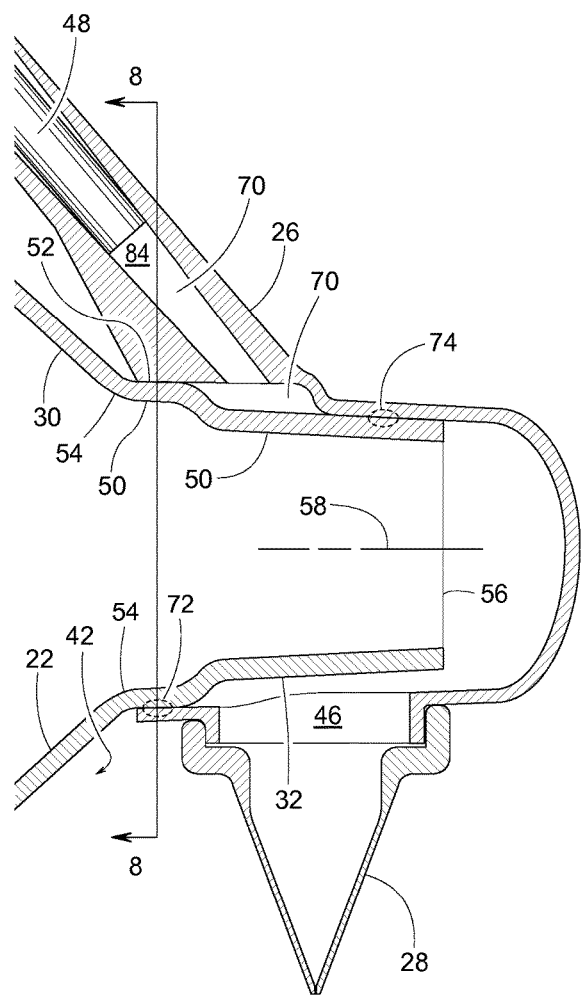
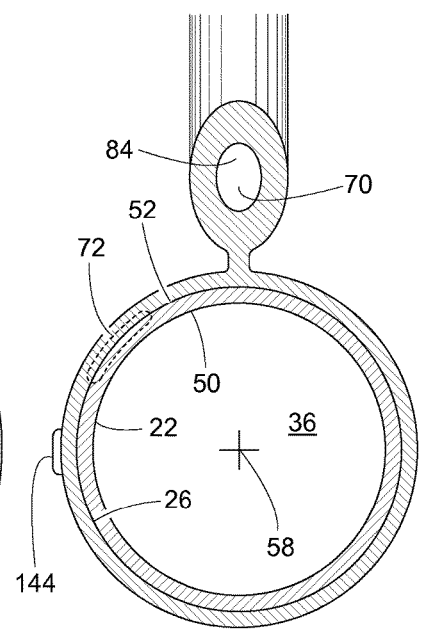

FIG. 9
FIG. 10
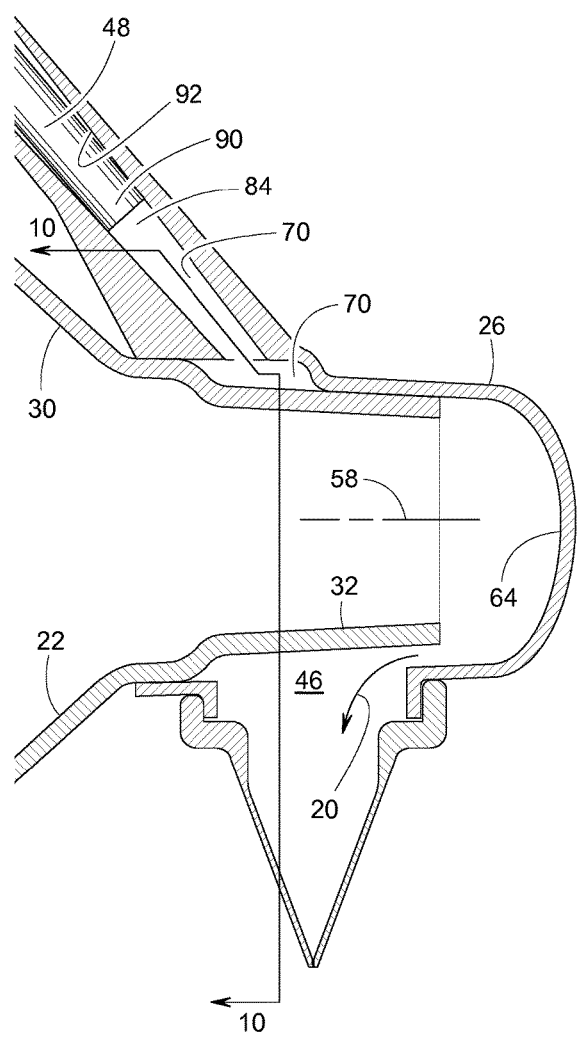
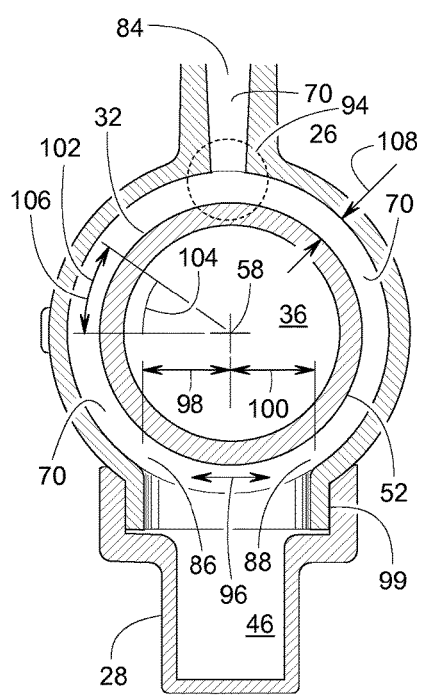

FIG. 11
FIG. 12
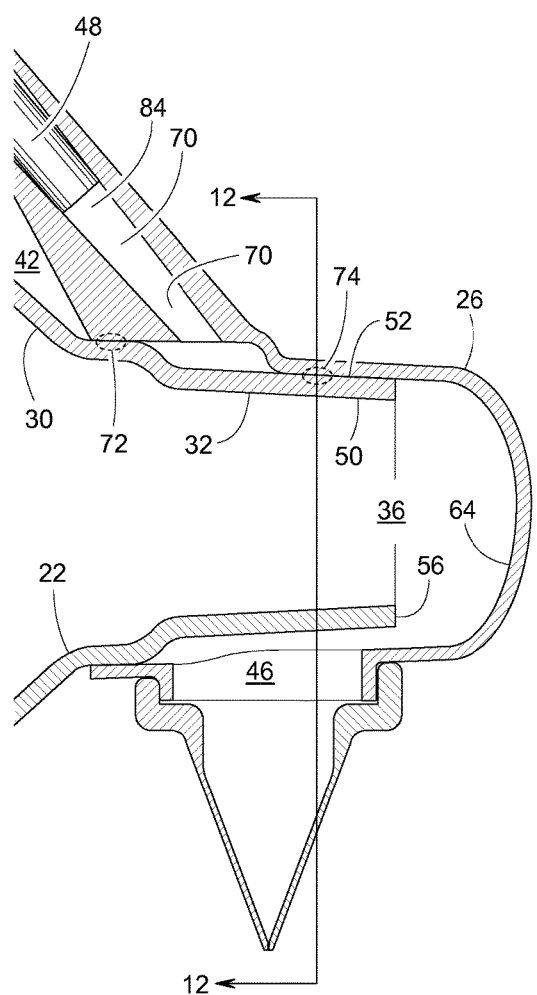
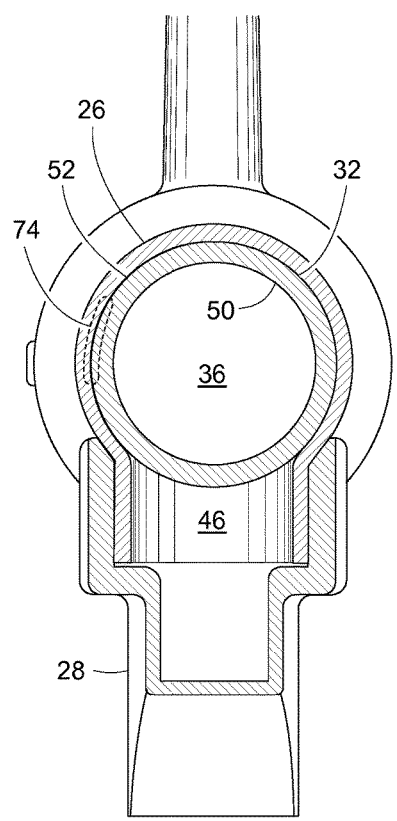

FIG. 13
FIG. 14
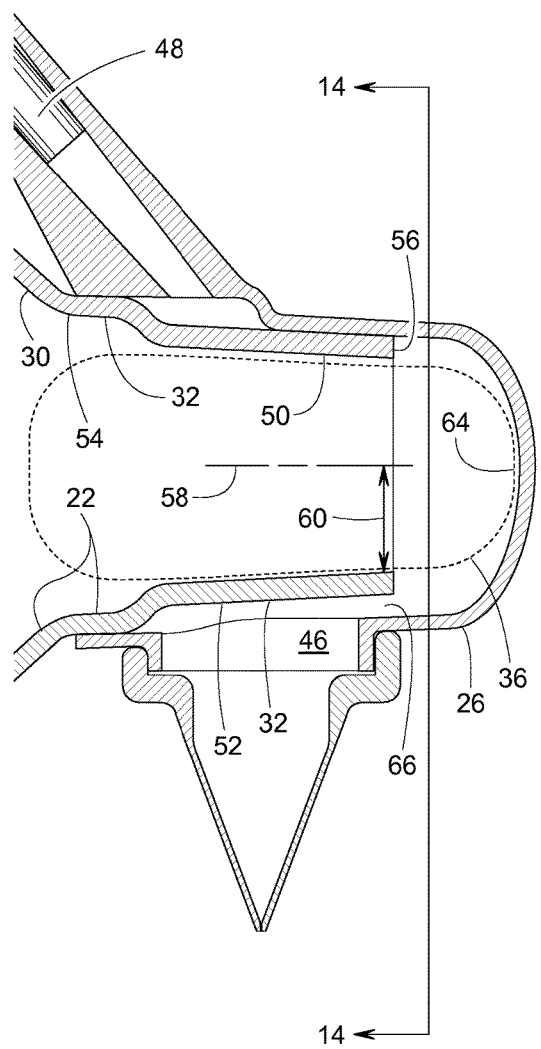
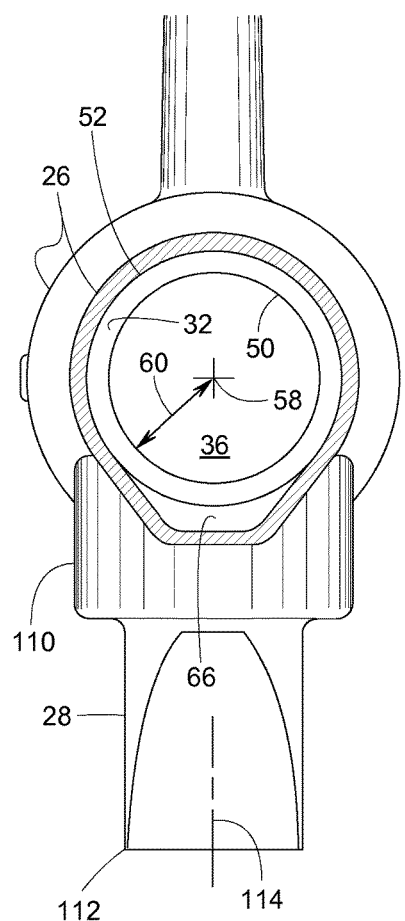

FIG. 15
FIG. 16
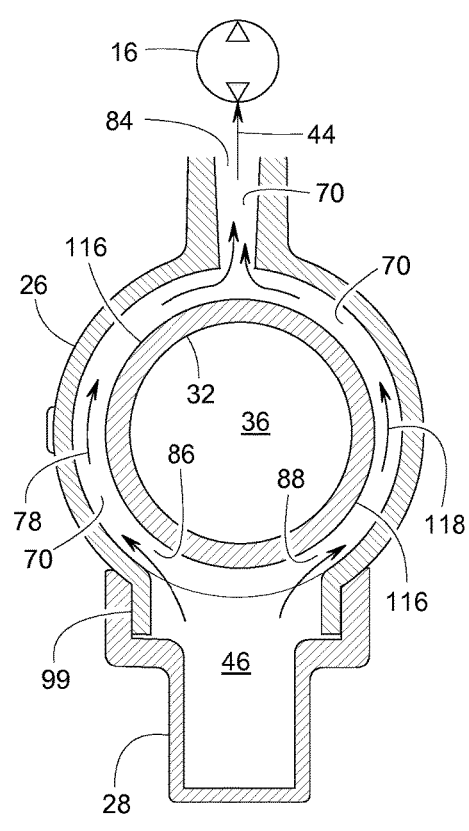
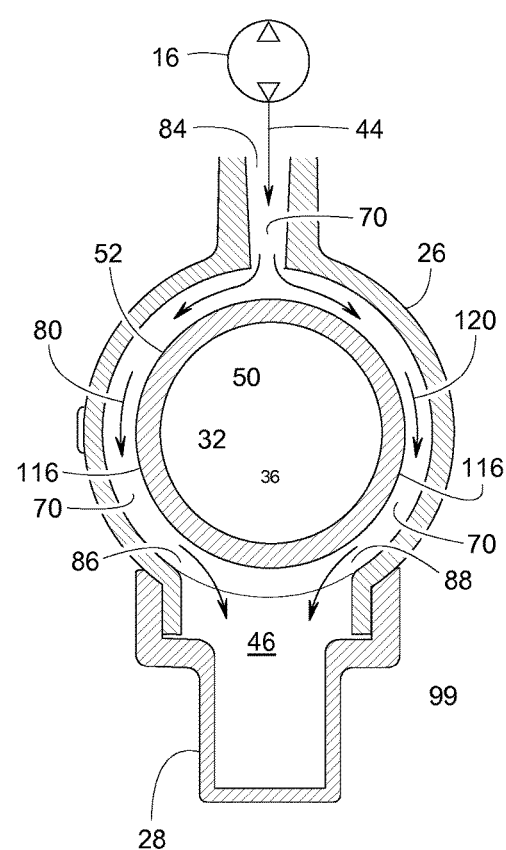

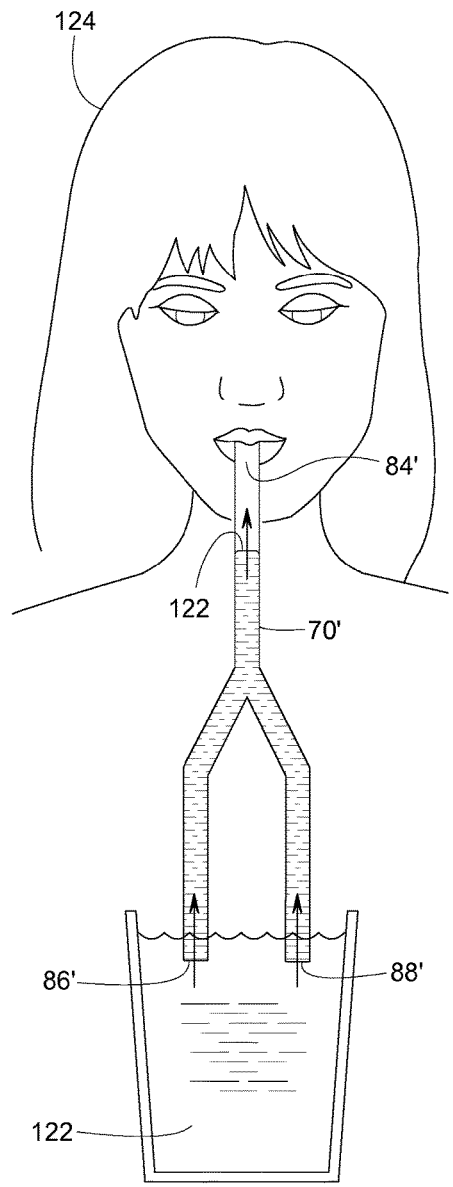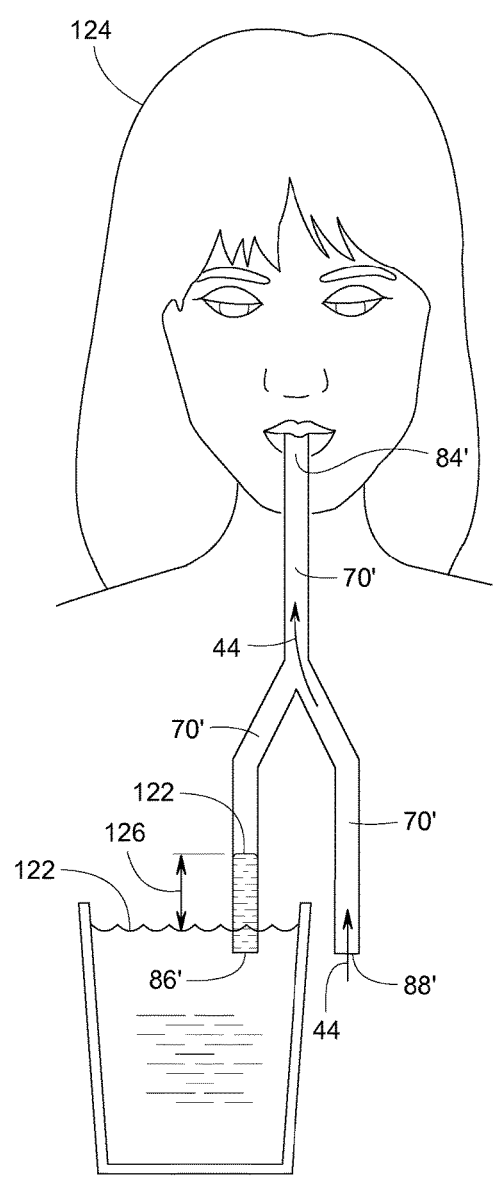

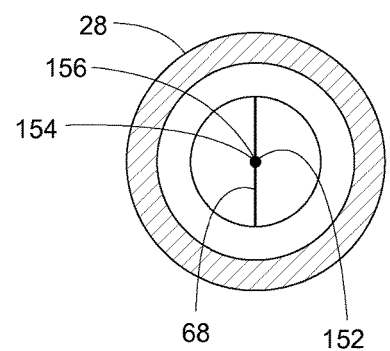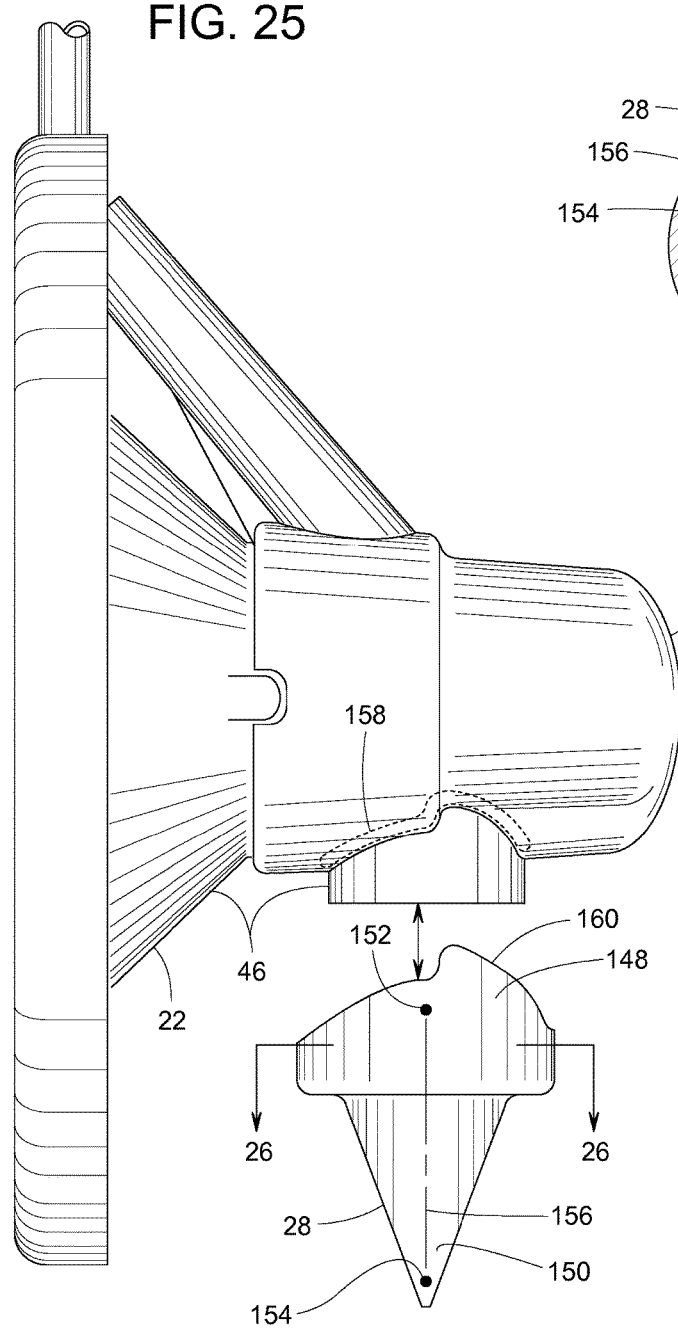
FIG. 25
FIG. 26

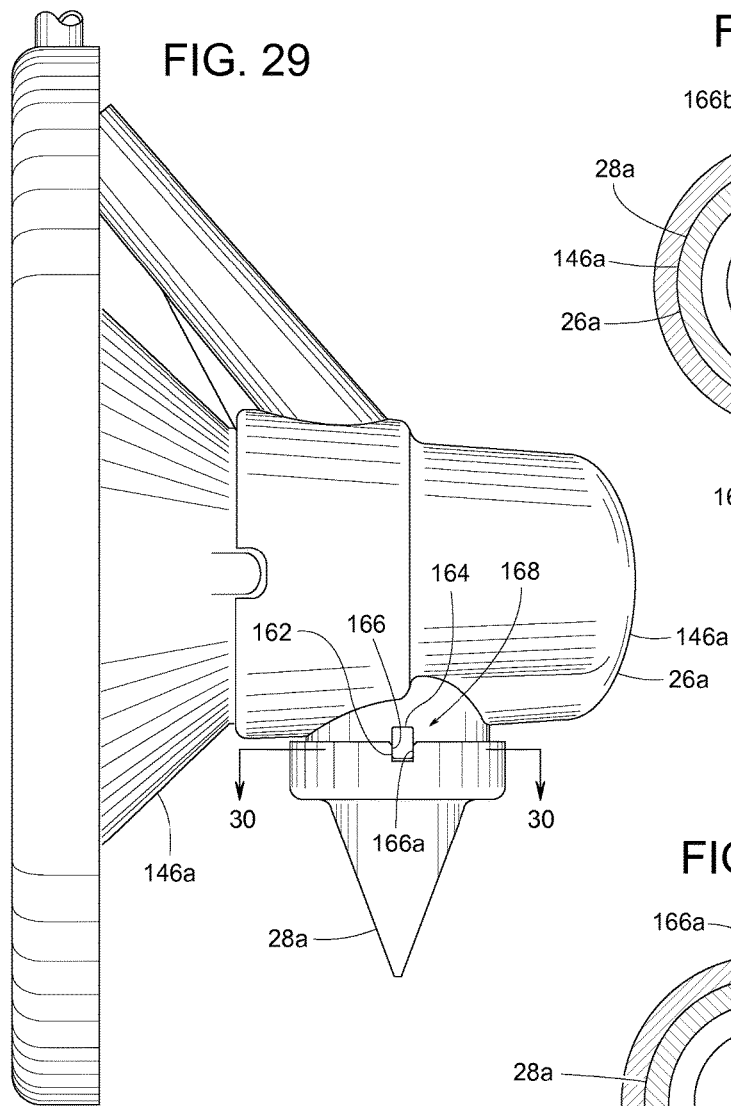
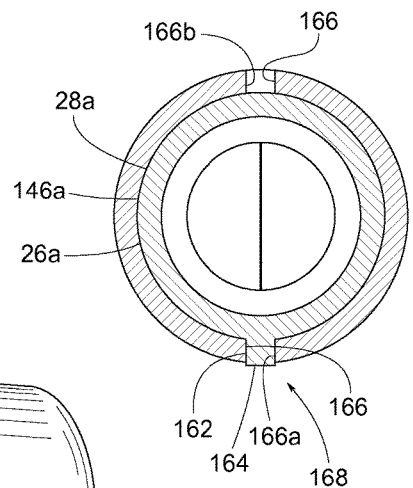
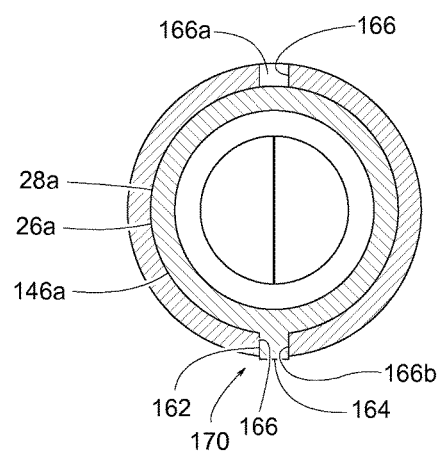

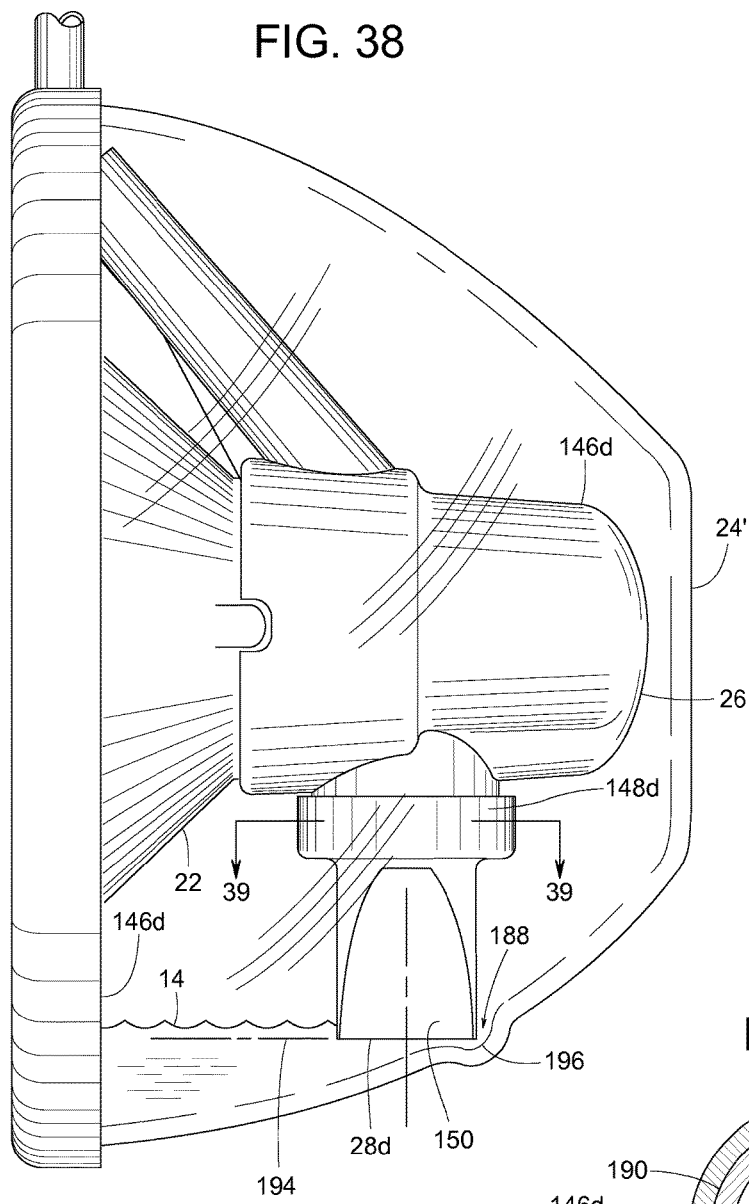
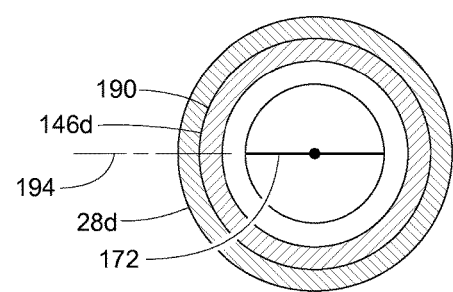

US 10,016,547 B2

FOOLPROOF VALVE ASSEMBLY FOR A BREAST MILK COLLECTOR

FIELD OF THE DISCLOSURE

The subject invention generally pertains to human breast milk collection devices and more specifically to means for ensuring proper assembly of such devices.

BACKGROUND

Breast pump systems are used for collecting breast milk expressed from a lactating woman. Some breast pump systems have a milk collection device with a funnel that fittingly receives the woman's breast. In many cases, a vacuum pump provides cyclical periods of positive and negative pressure to the milk collection device. During periods of negative pressure (subatmospheric pressure), vacuum delivered to the device withdraws a small discrete volume of milk from the breast and conveys that charge of milk to a small charging chamber. During each period of positive pressure, lightly pressurized air relaxes the breast momentarily and at the same time forces the charge of milk from the charging chamber to a larger milk storage chamber. The cycle repeats until the storage chamber is full or the woman is finished "pumping."

Some breast pump systems have a milk collection device that is worn within the cup of a common brassiere. Examples of such systems are disclosed in U.S. Pat. Nos. 7,559,915; 8,118,772; and 8,702,646; all of which are incorporated herein by reference

BRIEF DESCRIPTION OF THE DRAWINGS

FIG. 7 is a cross-sectional view showing a portion of FIG. 6.

FIG. 8 is a cross-sectional view taken along line 8-8 of FIG. 7.

FIG. 9 is a cross-sectional view showing a portion of FIG. 6.

FIG. 10 is a cross-sectional view taken along line 10-10 of FIG. 9.

FIG. 11 is a cross-sectional view showing a portion of FIG. 6.

FIG. 12 is a cross-sectional view taken along line 12-12 of FIG. 11.

FIG. 13 is a cross-sectional view showing a portion of FIG. 6.

FIG. 14 is a cross-sectional view taken along line 14-14 of FIG. 13.

FIG. 15 is a cross-sectional view similar to FIG. 10 but showing an airflow pattern during a negative pressure period (first period).

FIG. 16 is a cross-sectional view similar to FIG. 15 but showing an airflow pattern during a positive pressure period (second period).

FIGS. 17 and 18 are illustrations demonstrating an example "vacuum break" concept.

FIG. 25 is a side view similar to FIG. 24 but showing the valve in a cleaning position spaced apart from the assembly.

FIG. 26 is a cross-sectional view taken along line 26-26 of FIG. 25.

FIG. 29 is a side view similar to FIG. 24 but showing another example valve constructed in accordance with the teachings disclosed herein.

FIG. 30 is an enlarged cross-sectional view taken along line 30-30 of FIG. 29.

FIG. 31 is an enlarged cross-sectional view similar to FIG. 30 but showing the valve rotated 180 degrees.

FIG. 38 is a side view similar to FIG. 36 but showing the valve rotated 90 degrees.

FIG. 39 is a cross-sectional view taken along line 39-39 of FIG. 38.

DETAILED DESCRIPTION

Figure 19:
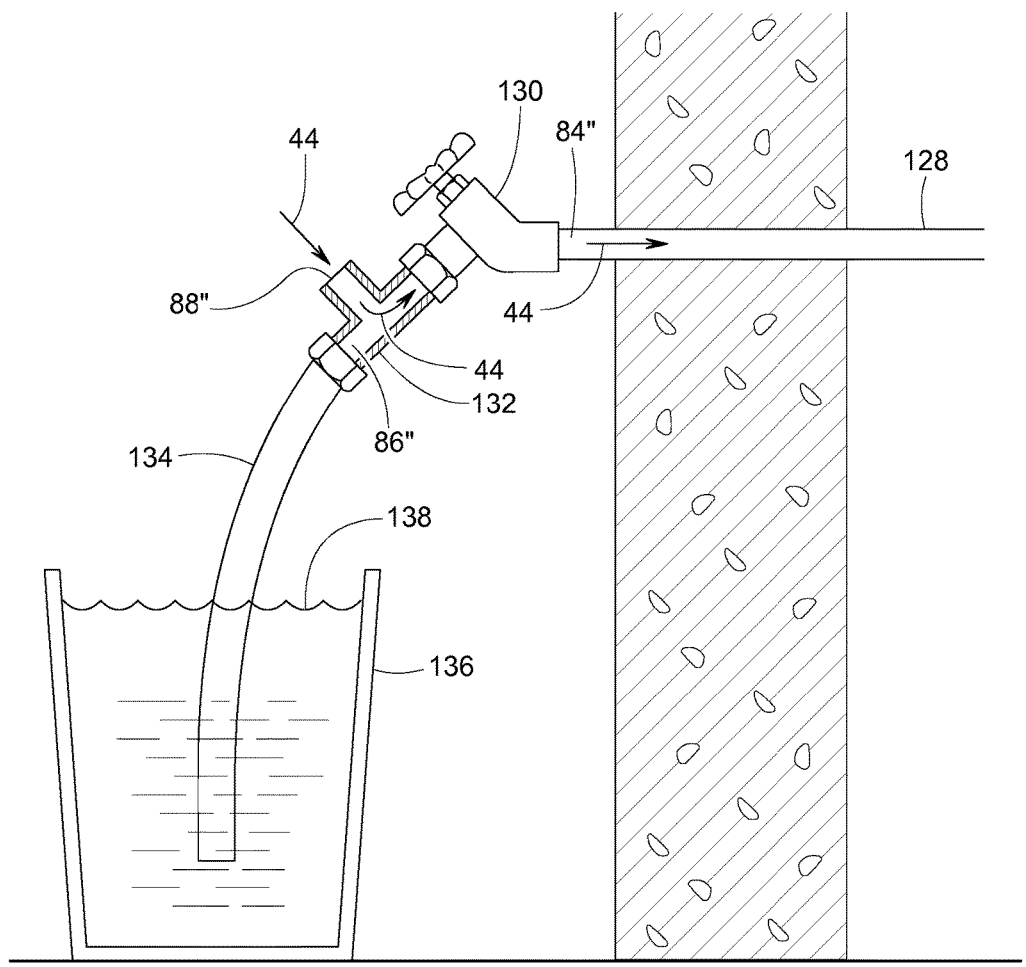
FIG. 19 is an illustration demonstrating another example "vacuum break" concept.
Figure 21:
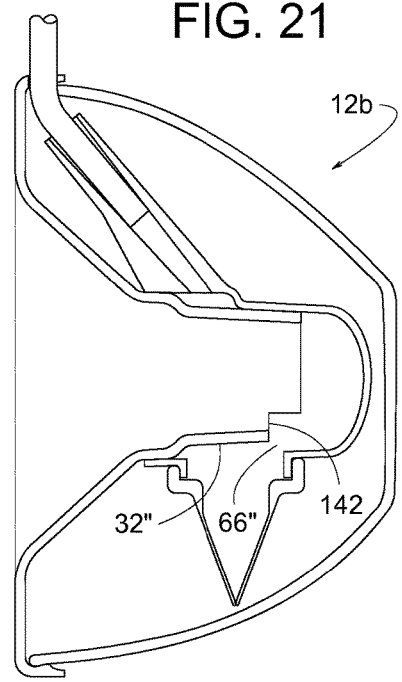
FIG. 21 is a cross-sectional view similar to FIG. 1 but showing another example milk collection device constructed in accordance with the teachings disclosed herein.
Figure 22:
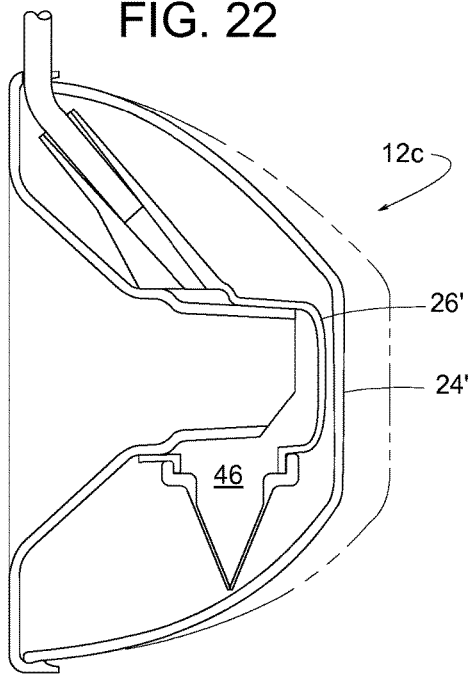
FIG. 22 is a cross-sectional view similar to FIG. 1 but showing of another example milk collection device constructed in accordance with the teachings disclosed herein.

FIGS. 1-16 show various views of an example breast pump system 10 that includes a milk collection device 12 with means for preventing milk 14 from backflowing to a vacuum pump 16. FIGS. 17-19 illustrate the underlying operating principle of vacuum breakers. And FIGS. 21-22 show variations of the system design. The general design isolates a subatmospheric air flow path 102 (FIG. 10) from a milk flow path 20 (FIG. 9) even if milk collection device 12 it tipped completely over (FIG. 4). The vacuum breaker concept keeps fluids separated without using conventional baffles, which inherently have crevices that can be difficult to clean.

Figure 1:
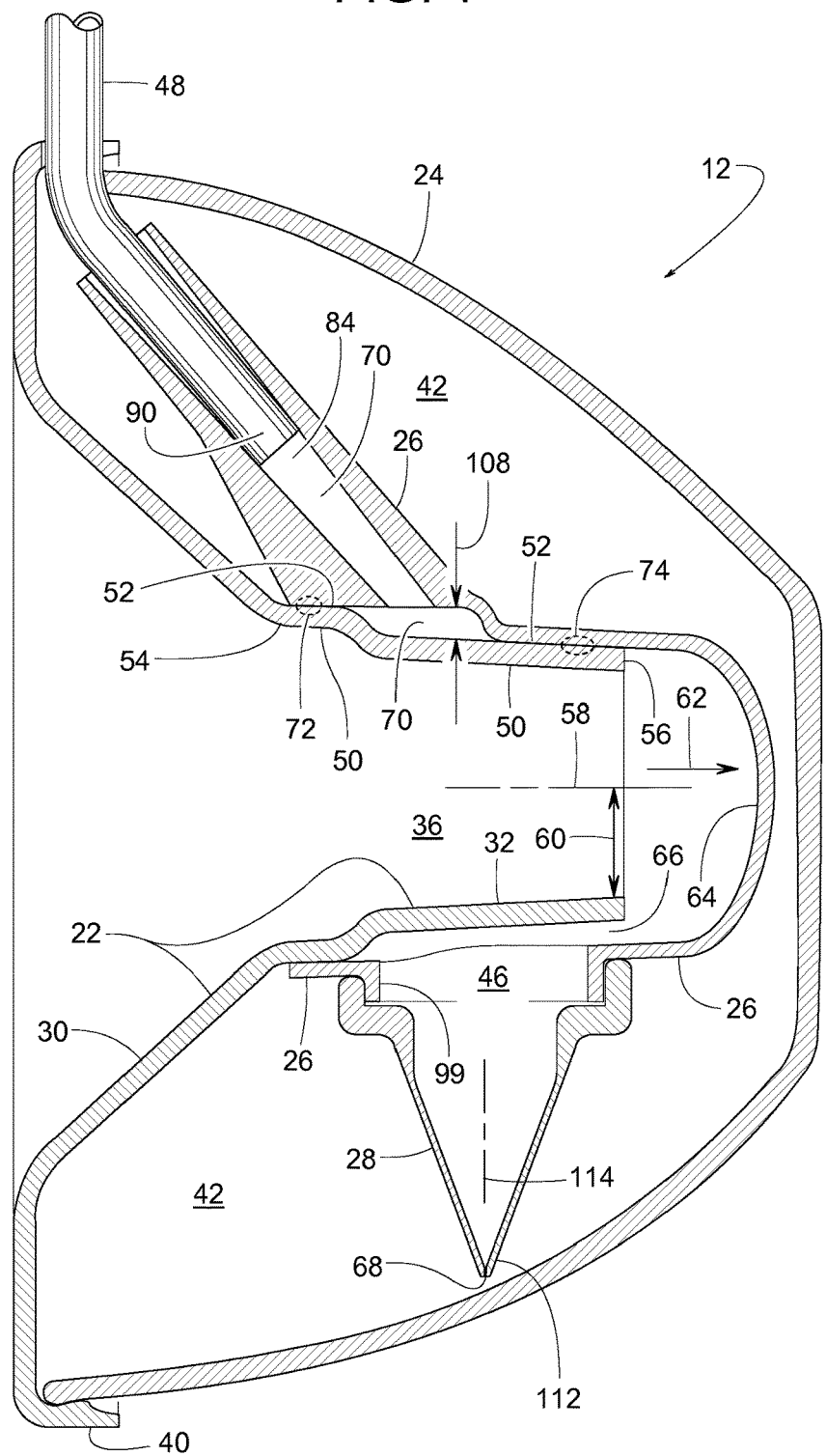
FIG. 1 is a cross-sectional side view of an example milk collection device constructed in accordance with the teachings disclosed herein.
Figure 5:
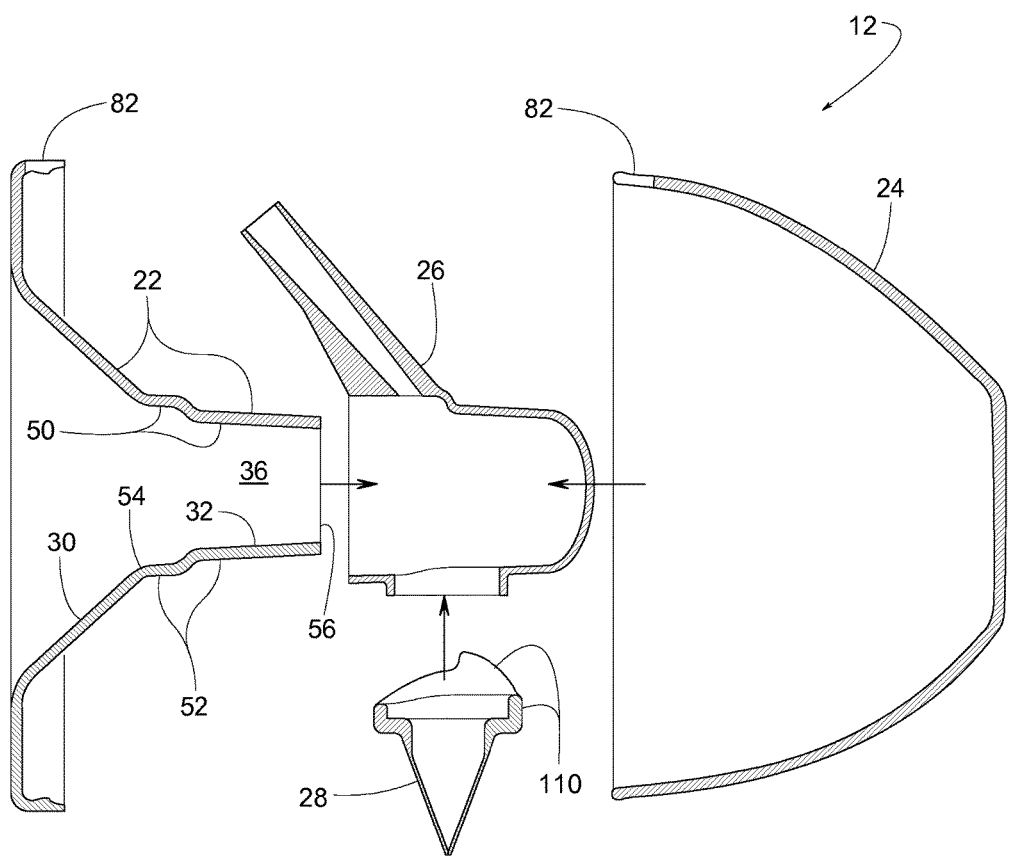
FIG. 5 is a cross-sectional view of the milk collection device shown in FIG. 1 but showing the device in a disassembled cleaning state.

As an overview of the breast pump system's general construction, milk collection device 12 comprises four main parts: a funnel-shaped breast receiver 22, a domed outer shell 24, a fluid exchanger 26, and a unidirectional valve 28 (e.g., a check valve, a duckbill check valve, a reed valve, a ball check valve, a diaphragm check valve, a swing check valve, etc.). FIG. 1 shows these for main parts in an assembled operating state with the parts being positioned as a unit in a predetermined orientation, and FIG. 5 shows them in a disassembled cleaning state. Breast receiver 22 itself comprises a breast guide 30 and a nipple receptacle 32. Breast guide 30 is generally conical for fittingly receiving a breast 34 of a lactating woman 36, and nipple receptacle 32 is tubular and defines a nipple chamber 36 for receiving a nipple 38 of breast 34.

In some examples, outer shell 24 removably connects to a flange 40 of breast receiver 22 to define a milk storage chamber 42 between outer shell 24 and breast receiver 22. Fluid exchanger 26 is coupled to breast receiver 22 to provide means for strategically directing milk 14 and air 44 within milk collection device 12. Valve 28 establishes a milk charging chamber 46 between nipple receptacle 36 and storage chamber 42. In some examples, charging chamber 46 is cycled between positive and negative pressure to draw discrete quantities of expressed milk from nipple receptacle 36. During periods of positive pressure, charging chamber 46 discharges each discrete quantity or charge through valve 28 to storage chamber 42.

To provide charging chamber 46 with air 44 cyclically at subatmospheric pressure and positive or atmospheric pressure, a suction tube 48 couples milk collection device 12 to vacuum pump 16. The term, "vacuum pump," refers to any device that provides subatmospheric pressure continuously, cyclically, or at least momentarily. Vacuum pump 16 is schematically illustrated to represent all types of vacuum pumps, examples of which include, but are not limited to, a diaphragm pump, a bellows pump, a piston pump, a reciprocating pump, a peristaltic pump, a positive displacement pump, a gear pump, a lobed rotor pump, a screw compressor, a scroll compressor, and a rotary vane pump.

The breast pump system's structure and operation can be further understood with additional definitions and explanations of some detailed features of the system. Nipple receptacle 36 has an inner curved wall surface 50, an outer curved wall surface 52, a proximate end 54 and a distal end 56. The nipple receptacle's tubular shape defines a longitudinal centerline 58 and nipple chamber 30. A minimum radial distance 60 exists between longitudinal centerline 58 and inner curved wall surface 50, wherein the minimum radial distance is measured perpendicular to centerline 58. Nipple receptacle 36 extends longitudinally in a forward direction 62 (parallel to centerline 58) from proximate end 54 to distal end 56. In some examples, nipple chamber 36 extends farther forward than distal end 56 of nipple receptacle 32; however, any part of nipple receptacle 32 that happens to extend farther forward than nipple chamber 36 is considered an extension beyond distal end 56 and thus is not considered the receptacle's distal end 56 itself. In some examples, the most forward point of nipple chamber 36 is at a domed concave surface 64 on fluid exchanger 26. Surface 64 being domed rather than flat makes fluid exchanger 26 easier to clean after fluid exchanger 26 is separated from breast receiver 22.

When breast receiver 22 and valve 28 are attached to fluid exchanger 26, the resulting assembly produces various fluid passages, chambers and sealing interfaces. Upon disassembly, the passages, chambers and sealing interfaces become more open for easier cleaning and sanitizing. Examples of such passages, chambers and sealing interfaces include charging chamber 46, nipple chamber 36, a milk passage 66 for conveying milk 14 from nipple chamber 36 to charging chamber 46, a valve outlet 68 that periodically discharges discrete volumes of milk 14 to storage chamber 42, an air duct 70 that connects suction tube 48 in fluid communication with charging chamber 46, a primary sealing interface 72, and a secondary sealing interface 74.

Figure 2:
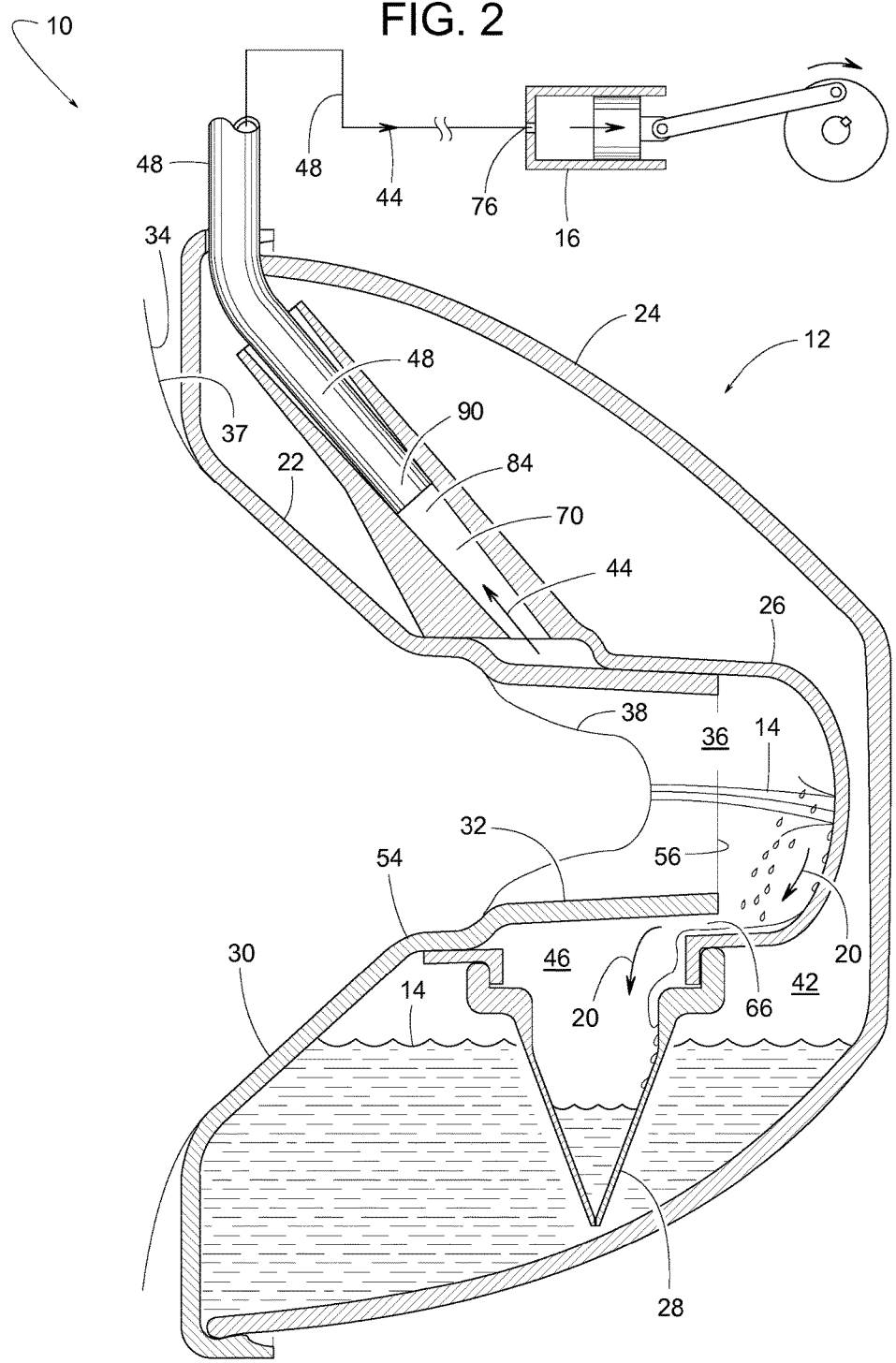
FIG. 2 is a combination schematic diagram and cross-sectional side view similar to FIG. 1 but showing the milk collection device as part of an example breast pump system.

In some examples, system 10 operates in an alternating manner of suction periods and pressurized periods. During suction periods, as shown in FIGS. 2 and 15, vacuum pump 16 applies suction or air at subatmospheric pressure to a remote end 76 of suction tube 48. At least some of the vacuum reaches nipple chamber 36 to draw milk expressed from nipple 38. The expressed milk 14 flows from nipple chamber 36, flows through milk passage 66, and collects at the bottom of charging chamber 46. The negative air pressure produced by vacuum pump 16 creates a first current of air 78 (FIG. 15) that effectively moves from nipple chamber 36 and effectively flows in series through milk passage 66, through charging chamber 46, through air duct 70 (FIGS. 9, 10, 15 and 16), through suction tube 48, and to vacuum pump 16. The terms, "effectively moves" and "effectively flows" means that there is some air movement from an upstream point toward a downstream point, but the air at the upstream point will not necessarily reach the downstream point, due to the travel distance and/or other flow constraints.

Figure 3:
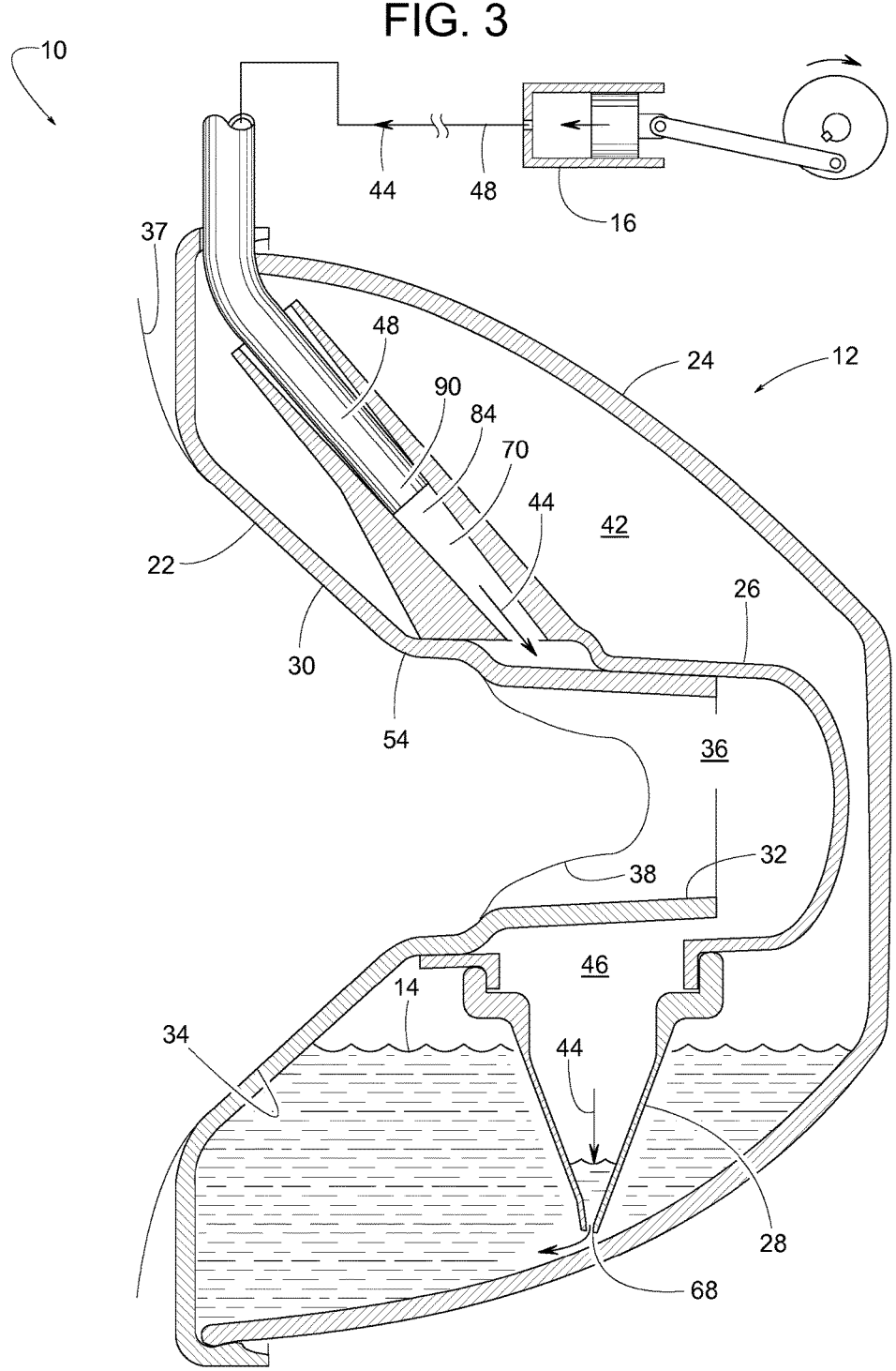
FIG. 3 is a view similar to FIG. 2 but showing the system during a positive pressure period rather than a suction pressure period.
Figure 4:
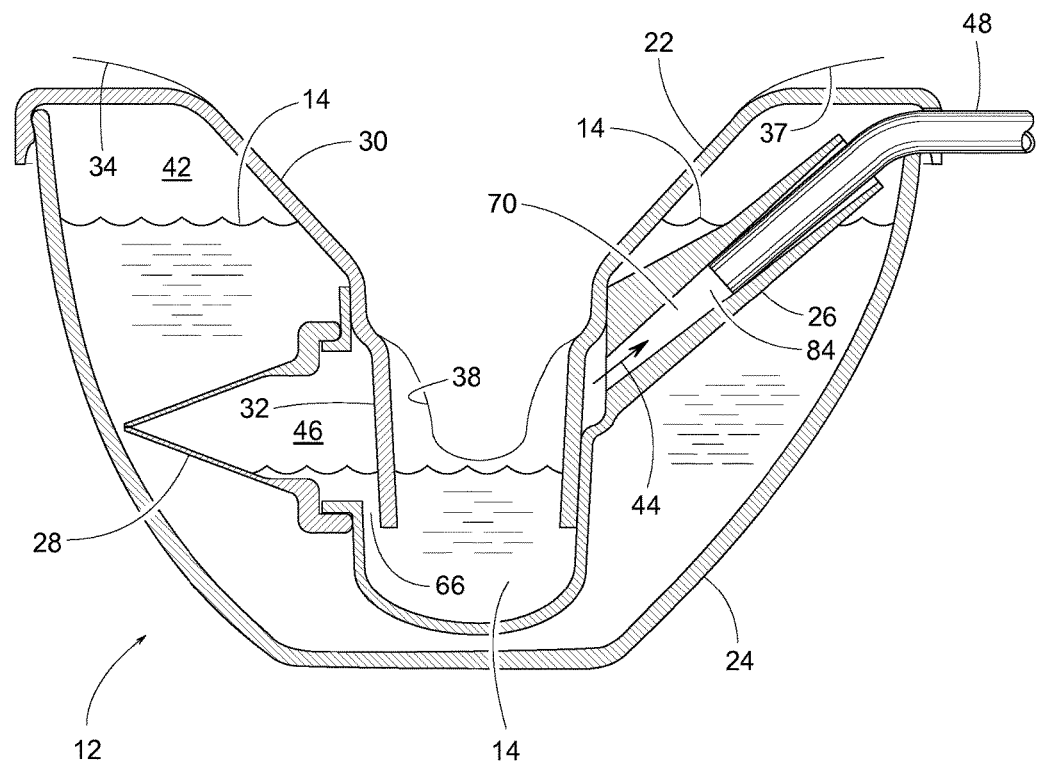
FIG. 4 is a cross-sectional side view of the milk collection device shown in FIGS. 1-3, but showing the device fully tipped over and pointed down.

During pressurized periods, as shown in FIGS. 3 and 16, vacuum pump 16 applies positive air pressure to suction tube 48. The positive pressure creates a second current of air 80 that effectively flows in series through suction tube 48, through air duct 70, through milk passage 66, and into nipple chamber 36. The air pressure in charging chamber 46 forces milk 14 (collected during the previous suction period) from charging chamber 46, down through valve 28, and into storage chamber 42. The air pressure in nipple chamber 36 allows breast 34 to relax prior to the next suction period.

The alternating cycle of suction and pressure is repeated for as long as desired or until storage chamber 42 is filled to some predetermined capacity. Upon completion of the pumping process, any suitable means can be used for transferring collected milk from storage chamber 42 to a bottle or to some other convenient storage container. One example method for transferring milk 14 from storage chamber 42 is to pull suction tube 48 out from within an opening 82 (FIG. 5) between breast receiver 22 and outer shell 24, and then pour collected milk 14 out through opening 82. Another method is to turn milk collection device 12 over (e.g., FIG. 4), remove breast receiver 22 from outer shell 24, and simply pour milk 14 out from shell 24.

Although FIG. 4 is referred to illustrate means for emptying milk 14 collected in storage chamber 42, the primary purpose of FIG. 4 is to show how well device 12 tolerates a completely tipped-over condition while still preventing milk 14 from backflowing into suction tube 48. Device 12 has three features that prevent milk backflow. One, in the tipped-over position, air duct 70 remains elevated above milk passage 66. Two, a circumferential seal 74 (FIG. 12) exists between air duct 70 and milk 14 in nipple chamber 36. Three, air duct 70 connects to charging chamber 46 at two spaced apart openings 86 and 88 (see FIG. 15 and the explanation referencing FIGS. 17, 18 and 19)

Preventing milk 14 from entering suction tube 48 is important for several reasons. Milk droplets or even a milk film trapped inside a narrow suction tube can be very difficult to thoroughly clean and sanitize. If left unclean, the trapped milk can contaminate future milk collections. Also, if milk in suction tube 48 migrates into vacuum pump 16, the milk can be even more difficult to remove and can possibly damage or destroy pump 16. Tolerating such unsanitized conditions is generally unheard of in the fields of medicine and food processing.

Figure 6:
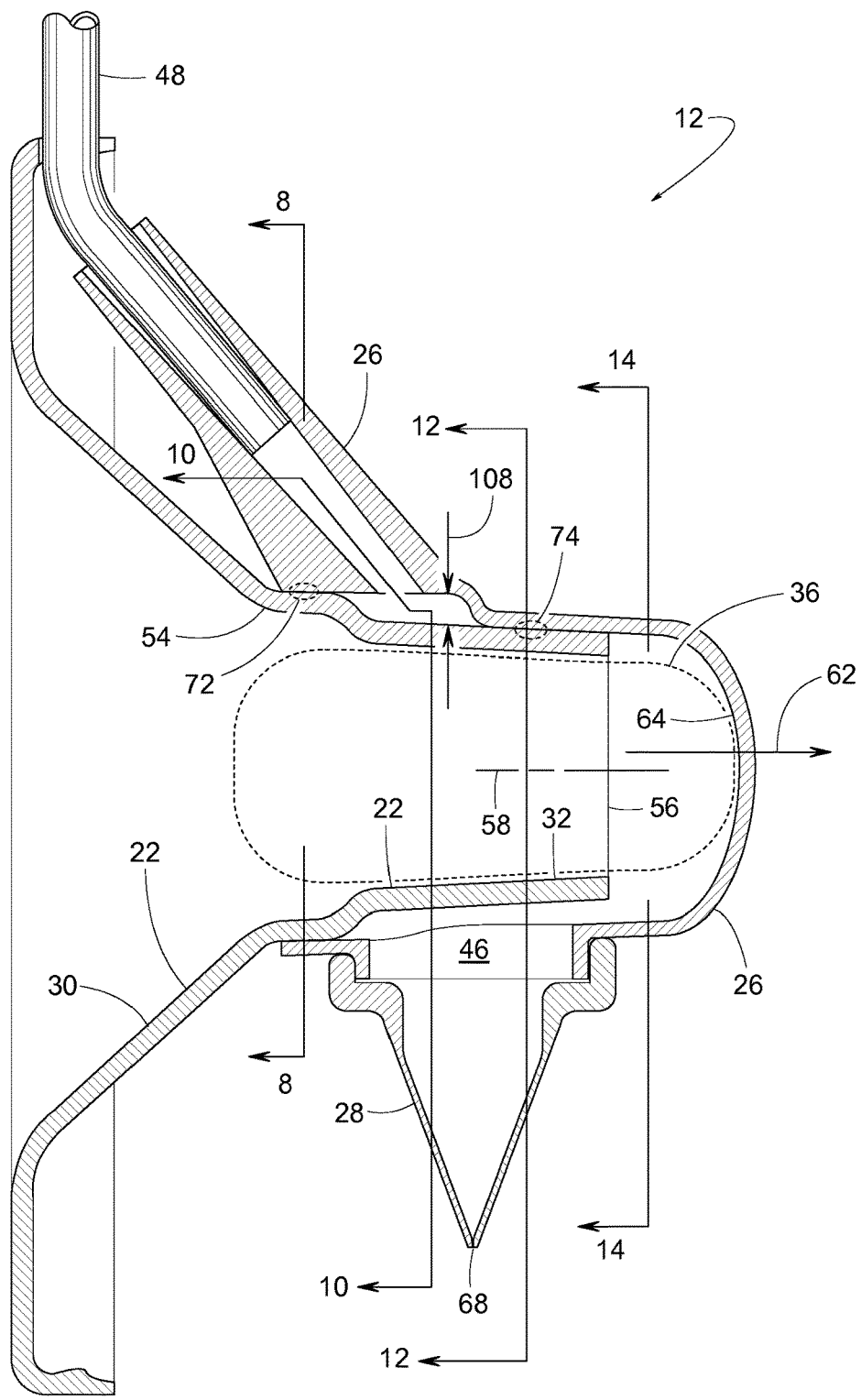
FIG. 6 is a cross-sectional view similar to FIG. 1 but with the outer shell omitted.

FIG. 6 serves as somewhat of an index drawing for a subsequent series of cross-sectional views. The views in the series are shown in sets of two and are identified as FIGS. 7-8, FIGS. 9-10, FIGS. 11-12, and FIGS. 13-14. FIGS. 7-8 show primary sealing interface 72 between an outer diameter of breast receiver 22 and an inner diameter of fluid exchanger 26. Primary sealing interface 72 is a relatively tight seal that extends 360 degrees circumferentially around centerline 58 to isolate localized pressure or vacuum within charging chamber 46 while the surrounding storage chamber 42 is at atmospheric pressure. In some examples, to ensure a positive seal, interface 72 tapers at 3-degrees in a lengthwise direction with reference to centerline 58.

FIGS. 9-10 show one example of air duct 70 connecting vacuum tube 48 in fluid communication with charging chamber 46. In this example, air duct 70 comprises a supply port 84 at a connection end 90 of suction tube 48, a first opening 86 at charging chamber 46, and a second opening 88 at charging chamber 46. To connect tube 48 to supply port 84, connection end 90 of suction tube 48 press-fits into a tapered bore 92 of fluid exchanger 26. A fork 94 (e.g., one path leading to two) in air duct 70 connects supply port 84 in fluid communication with openings 86 and 88. Features 84, 86 and 88 of FIG. 10 correspond respectively to points 84', 86' and 88' of FIG. 18. Features 84, 86 and 88 of FIG. 10 also correspond respectively to points 84", 86" and 88" of FIG. 19.

To apply the "vacuum break" concept illustrated in FIGS. 17 and 18, fork 94 straddles nipple receptacle 36 so that openings 86 and 88 are spaced apart in a lateral direction 96 with the nipple receptacle longitudinal centerline 58 being laterally interposed between openings 86 and 88 (dimensions 98 and 100). In some examples, nipple receptacle 36 is flanked by openings 86 and 88, which means that the nipple's longitudinal centerline 58 is laterally between openings 86 and 88, as shown in FIG. 10. The spaced-apart distance and elevation of openings 86 and 88 can be increased by increasing the diameter of a flange 99 to which valve 28 is attached.

Still referring to FIG. 10, some examples of air duct 70 define a flow path 102 from supply port 84 to first opening 86, wherein a curved section of flow path 102 extends circumferentially an angular distance 104 of at least thirty degrees to avoid having to create an alternate flow path in front of or through nipple chamber 36. In some examples, at least one section 106 of flow path 102 lies within a radial gap 108 between fluid exchanger 26 and the nipple receptacle's outer curved wall surface 52. Upon disassembling device 12 to its disassembled cleaning state (FIG. 5), section 106 of flow path 102 is split apart, which makes flow path 102 and air duct 70 much more accessible for cleaning.

FIGS. 11 and 12 show secondary sealing interface 74 radially between fluid exchanger 26 and the nipple receptacle's outer curved wall surface 52. Secondary sealing interface 74 provides a barrier that prevents milk 14 from flowing directly from nipple chamber 36 to air duct 70. FIG. 11 shows air duct 70 being between primary sealing interface 72 and secondary sealing interface 74.

Primary sealing interface 72 is the more critical seal of the two because primary sealing interface 72 is subjected to an appreciable pressure differential between supply port 84 and storage chamber 42. Secondary sealing interface 74, however, is not as critical because the pressure differential between supply port 84 and nipple chamber 36 is nearly zero. Consequently, in some examples, primary sealing interface 72 is made to be a tighter seal than secondary sealing interface 74. In other words, when breast receiver 22 is snugly inserted into fluid exchanger 26, the radial forces at primary sealing interface 72 is greater than that at secondary sealing interface 74.

It can be important to have primary sealing interface 72 be the dominant seal because when breast receiver 22 is inserted into fluid exchanger 26, something has to "bottom out" first to stop the relative insertion movement of breast receiver 22 into fluid exchanger 26. If secondary sealing surface 74 or distal end 56 abutting domed surface 64 were to be the first parts to bottom out, that might leave some radial clearance or leak path at primary sealing interface 72. Intentionally making primary sealing interface 72 be the first to bottom out, loosens the manufacturing tolerances at other near bottom-out locations, thus increasing assembly reliability, reducing tooling costs, and simplifying manufacturing.

FIGS. 13 and 14 show milk passage 66 between charging chamber 46 and nipple chamber 36. FIGS. 14 and 5 show how an irregular shaped upper flange 110 of valve 28 serves as a means for "clocking" or rotationally aligning valve 28 to fluid exchanger 26. Such alignment can be important to avoid interference between a lower end 112 of valve 28 and outer shell 24. For instance, if valve 28 were rotated ninety degrees (about a vertical axis 114) from the position shown in FIG. 1, the valve's lower end 112 might press up against outer shell 24, whereby outer shell 24 might hold valve 28 open and prevent it from closing.

FIGS. 15 and 16 illustrate an example breast pump method operating during a first suction period (FIGS. 2 and 15) and a second pressure period (FIGS. 3 and 16). FIG. 15 shows during the first period, directing first current of air 78 in a first curved upward direction circumferentially across a first outer convex wall surface 116 of nipple receptacle 32. FIG. 15 also shows during the first period, directing a third current of air 118 in a second curved upward direction circumferentially across the nipple receptacle's first outer convex wall surface 116. FIG. 16 shows during the second period, directing second current of air 80 in a first curved downward direction circumferentially across the nipple receptacle's first outer curved wall surface 116. FIG. 16 also shows during the second period, directing a fourth current of air 120 in a second curved downward direction circumferentially across the nipple receptacle's first outer curved wall surface 116, wherein nipple receptacle 32 is interposed between first current of air 78 and third current of air 118 during the first period, and nipple receptacle 32 is interposed between second current of air 80 and fourth current of air 120 during the second period.

FIGS. 17 and 18 illustrates the concept of a vacuum breaker as a means for preventing a liquid 122 from back-flowing up to a suction source 124. Liquid 122 only reaches suction source 124 when both openings 86' and 88' are submerged in liquid 122, as shown in FIG. 17. If only one opening 86' is submerged and the other opening 88' is exposed to air 44, as shown in FIG. 18, air 44 readily supplies the volume drawn in by suction source 124. Through a given opening, air can flow about thirty times easier than water. Consequently, only a slight pressure differential is needed for air 44 to rush through opening 88' to suction source 124. That slight pressure differential creates only a slight pressure head 126 that is unable to lift liquid 122 from opening 86' to suction source 124.

FIG. 19 provides another example of illustrating a vacuum breaker concept. This example involves the use of a residential water line 128, an outdoor faucet 130, a simplified vacuum breaker 132, and a garden hose 134 partially submerged in a bucket 136 of contaminated water 138. In this example, if unusual adverse conditions create a vacuum in water line 128, clean outdoor air 44 rather than contaminated water 138 will be drawn into water line 128.

Figure 20:
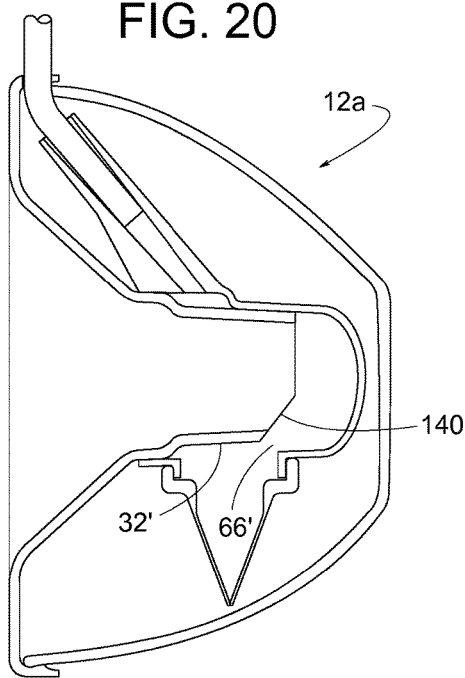
FIG. 20 is a cross-sectional view similar to FIG. 1 but showing another example milk collection device constructed in accordance with the teachings disclosed herein.

FIGS. 20, 21 and 22 show various design modifications. FIG. 20 shows an altered milk passage 66' created by a beveled edge 140 at the end of a nipple receptacle 32'. FIG. 21 shows an altered milk passage 66" created by a notched edge 142 at the end of a nipple receptacle 32". FIG. 22 shows that a stubbier fluid exchanger 26' and a less protruding outer shell 24' can be used when air duct 70 curves around the sides of the nipple receptacle rather than in front of it. The stubbier fluid exchanger 26' also reduces the effective volume of charging chamber 46, which can be beneficial when using certain low displacement vacuum pumps.

Figure 23:
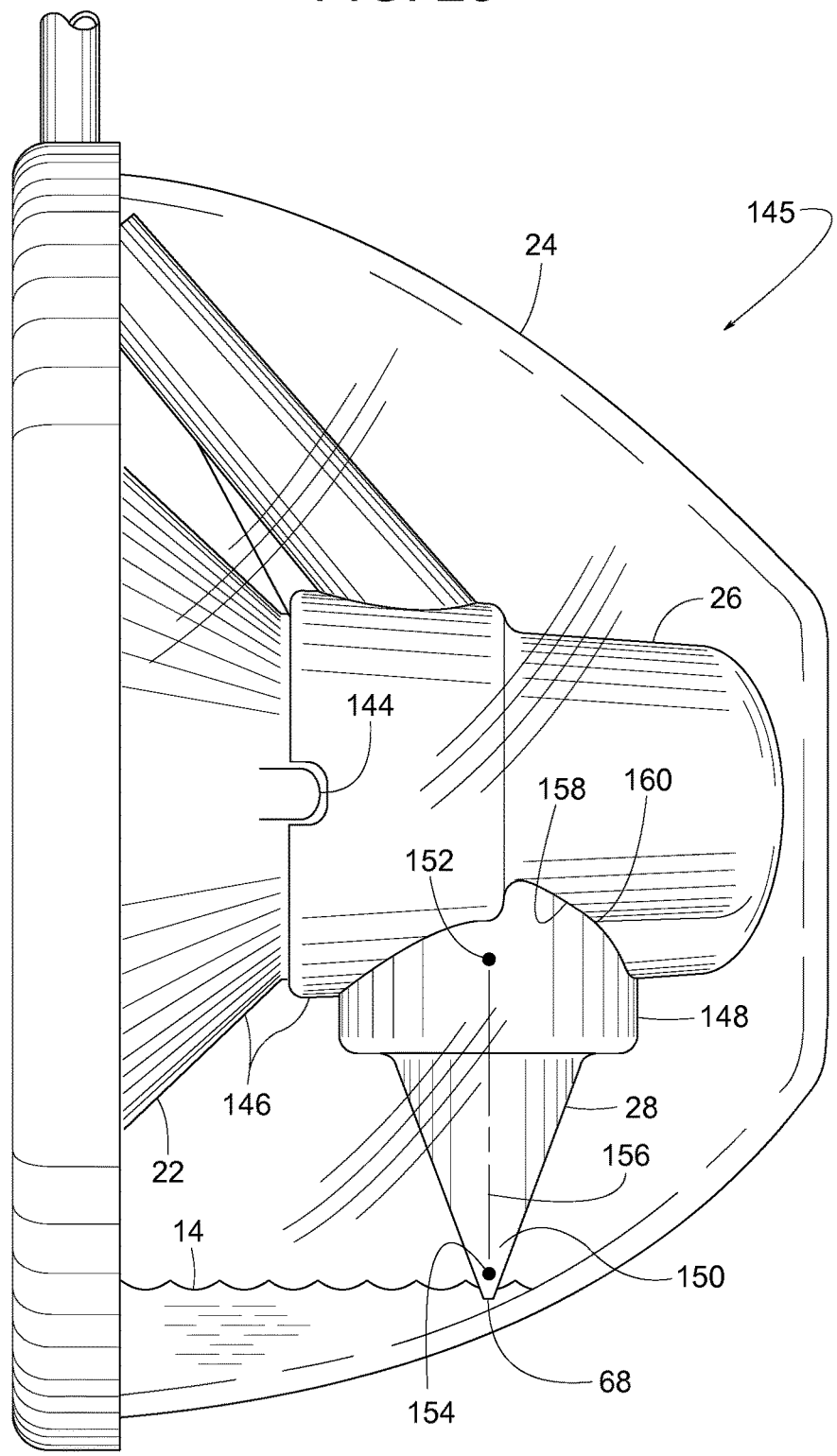
FIG. 23 is a side view of the milk collection device shown in FIG. 1.
Figure 24:
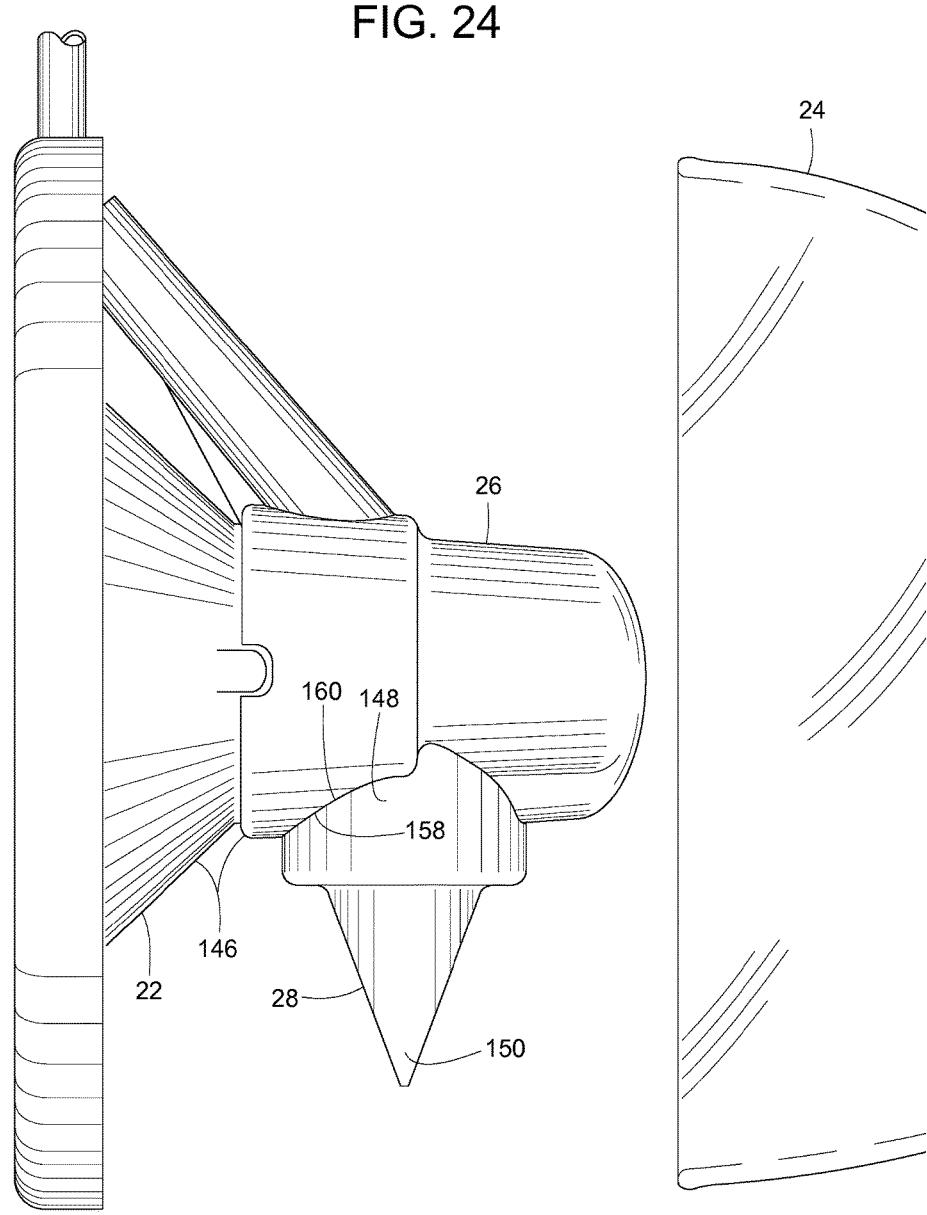
FIG. 24 is a side view similar to FIG. 24 but showing an outer shell separated from the rest of the milk collection device and showing an example valve in a first operating position attached to an example assembly.
Figure 27:
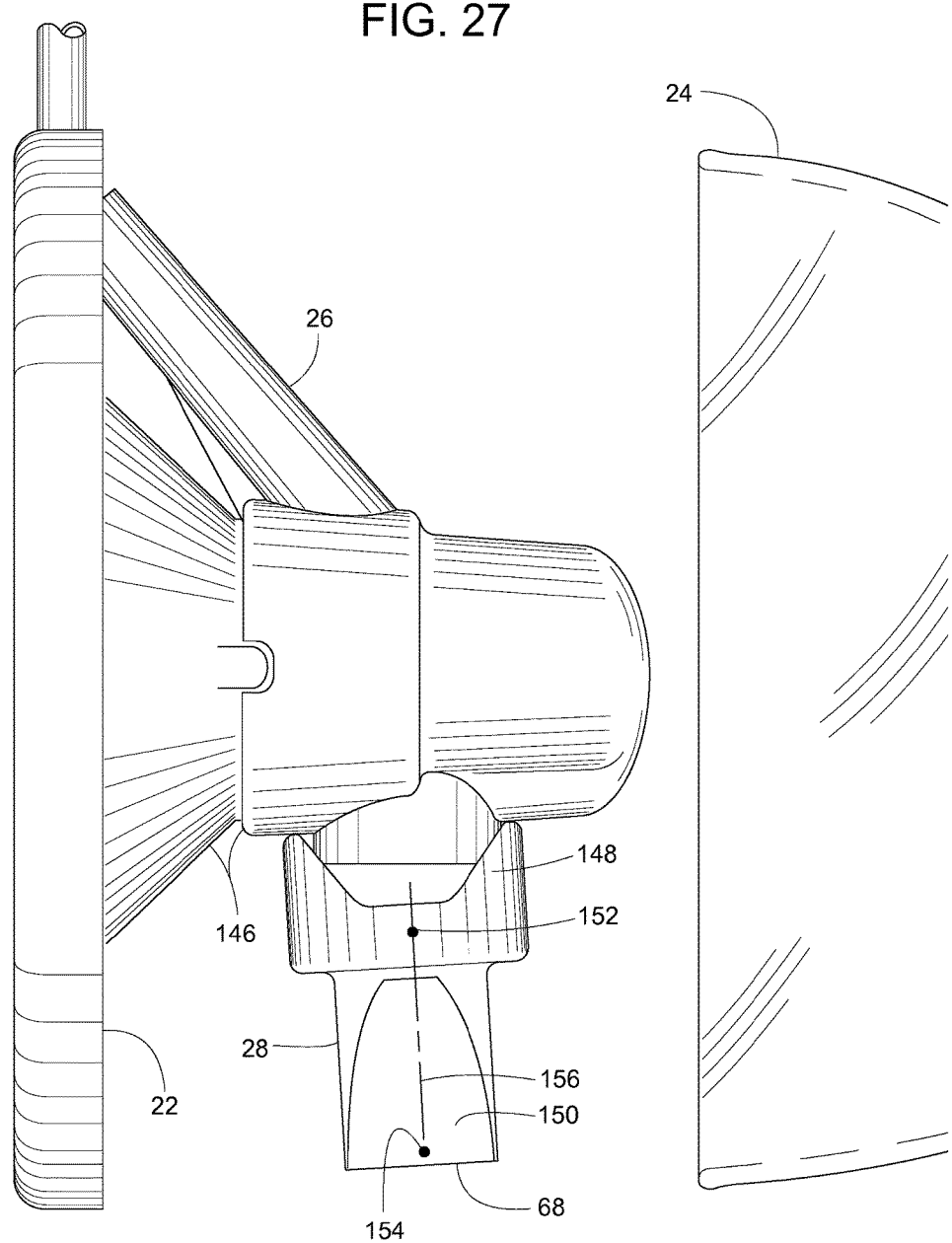
FIG. 27 is a side view similar to FIG. 24 but showing the valve in a rotationally displaced position.
Figure 28:
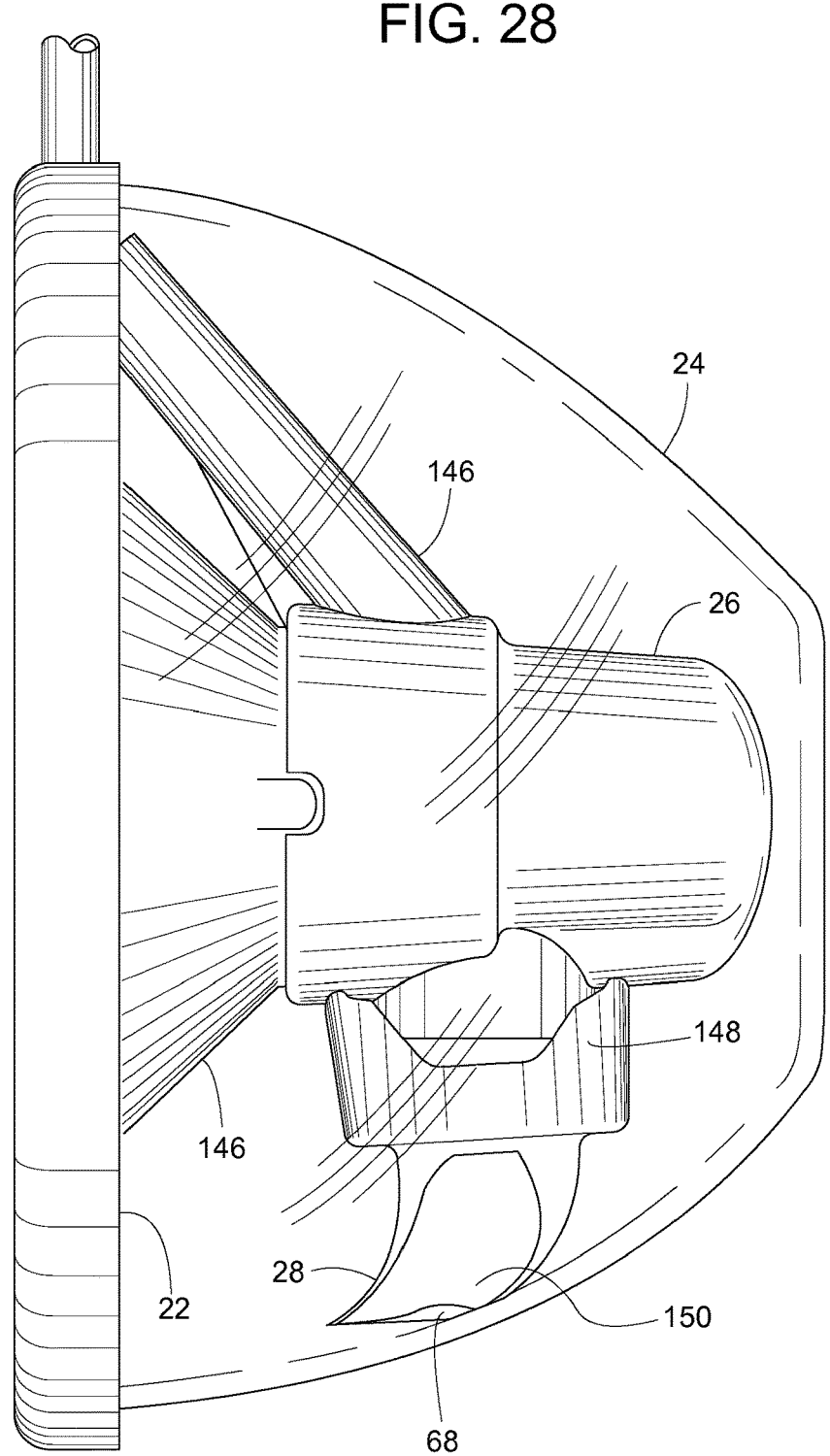
FIG. 28 is a side view similar to FIG. 27 but showing the outer shell attached to the assembly and interfering with the valve.

FIGS. 23-28 show breast pump system 145 with particular focus on valve 28 and the way it connects to an assembly 146, wherein assembly 146 is comprised of fluid exchanger 26 and breast receiver 22. In the illustrated example, valve 28 connects to fluid exchanger 26 of assembly 146. FIG. 23 shows outer shell 24 attached to breast receiver 22 and also shows valve 28 in a first operating position attached to assembly 146. FIG. 24 shows outer shell 24 disconnected from assembly 146. FIG. 25 shows valve 28 at a cleaning position disconnected from assembly 146. FIGS. 27 and 28 show valve 28 at a rotationally displaced position engaging assembly 146.

In the example where valve 28 is a duckbill-style valve (e.g., FIGS. 1 and 23-38), there are some benefits to having valve outlet 68 positioned near the lower inner wall surface of outer shell 24. The benefits may include, but are not necessarily limited to, providing for a more compact milk collection device and increasing the likelihood that outlet 68 is submerged in milk 14. Duckbill-style valves tend to close more readily when the fluid downstream of its outlet is liquid rather than gas because for a given opening (e.g., outlet 68), air can pass through about thirty times easier than water, so a backflow of air might occur without valve 28 reactively closing upon it. In some examples, even a few drops of liquid downstream of outlet 68 can be sufficient for valve 28 to snap shut in reaction to a backflow pressure differential across valve 28.

Valve 28 includes an attachment end 148 and a discharge end 150. Attachment end 148 defines an attachment end central point 152 centrally located at attachment end 148. Discharge end 150 defines a discharge end central point 154 centrally located at discharge end 150. Valve 28 defines a longitudinal centerline 156 passing through central points 152 and 154. Valve 28 is positioned selectively in a first operating position (FIGS. 23 and 24) and a cleaning position (FIG. 25), wherein attachment end 148 is connected to assembly 146 when valve 28 is in the first operating position, and attachment end 148 is spaced apart from assembly 146 when valve 28 is in the cleaning position. The drawings show that assembly 146 is closer to attachment end 148 than to discharge end 150 when valve 28 is in the first operating position, and discharge end 150 is proximate outer shell 24 when breast receiver 22 is coupled to outer shell 24 while valve 28 is in the first operating position.

To ensure that valve 28 is properly attached to assembly 146, assembly 146 has a first mating surface 158 and attachment end 148 of valve 28 has a second mating surface 160. When valve 28 is properly installed at the first operating position, mating surfaces 158 and 160 are rotationally interlocked at a first predetermined rotational position (FIGS. 23 and 24) about the valve's longitudinal centerline 156. In the example shown in FIGS. 24 and 25, first mating surface 158 is an exterior contour of assembly 146 that matingly engages second mating surface 160, which is a nonplanar axial surface on the valve's attachment end 148 and faces toward assembly 146. To provide an anti-rotation interlock without relying on friction alone, some examples of valve 28 have at least portions of second mating surface 160 that are not perpendicular to the valve's longitudinal centerline 156.

If valve 28 is improperly attached to assembly 146 at a rotationally displaced position (e.g., FIGS. 27 and 28), the valve's discharge end 150 adversely engages outer shell 24, as shown in FIG. 28. In some examples, such engagement between the valve's discharge end 150 and outer shell 24 can distort valve 28 to a point where valve outlet 68 is held continuously open. However, when valve 28 is in the first operating position while breast receiver 22 is coupled to outer shell 24, the valve's discharge end 150 is spaced apart from outer shell 24, as shown in FIG. 23, whereby valve outlet 68 can open and close normally.

FIGS. 29-35 show examples of valves that can be further positioned selectively to a second operating position. In the example shown in FIGS. 29-31, a valve 28a can be positioned selectively to a first operating position (FIGS. 29 and 30) and to a second operating position (FIG. 31). In this example, assembly 146a has a first mating surface 162 in the form of a protrusion 164 extending radially from fluid exchanger 26a. Valve 28a has a second mating surface 166 in the form of two slots 166a and 166b. Depending on the rotational position of valve 28a, protrusion 164 can engage slot 166a or 166b. When valve 28a is in the first operating position, protrusion 164 in slot 166a provides a first key-in-slot engagement 168 that interlocks the rotational position of valve 28a relative to assembly 146a. When valve 28a is in the second operating position, about 180 degrees from the first operating position, protrusion 164 in slot 166b provides a second key-in-slot engagement 170 that interlocks the rotational position of valve 28a relative to assembly 146a. With valve 28a in either the first operating position (FIG. 30) or 180 degrees from that at the second operating position (FIG. 31), in either position, an elongate slit 172 (valve outlet 68) lies in a direction that avoids interference between outer shell 24 and the valve's discharge end 150.

Figure 32:
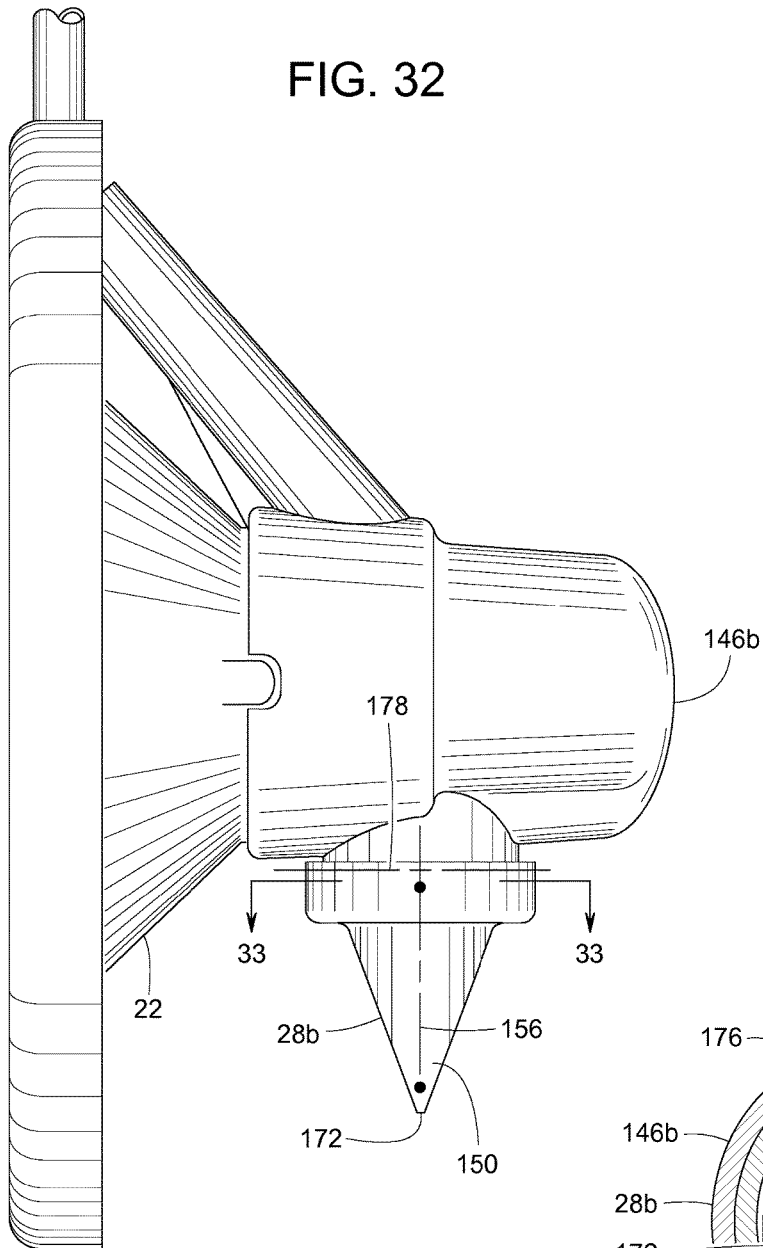
FIG. 32 is a side view similar to FIG. 24 but showing another example valve constructed in accordance with the teachings disclosed herein.
Figure 33:
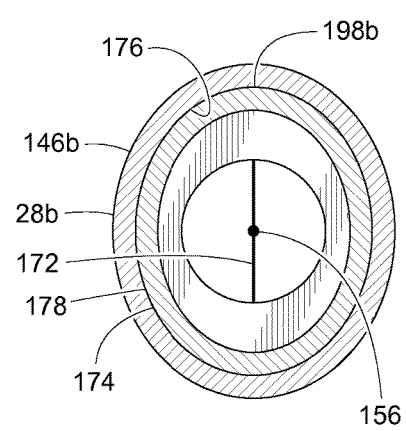
FIG. 33 is an enlarged cross-sectional view taken along line 33-33 of FIG. 32.

In the example shown in FIGS. 32 and 33, a valve 28b can be positioned relative to assembly 146b selectively to a first operating position (FIGS. 32 and 33) and to a second operating position. The second operating position is 180 degrees from the first one, so FIGS. 32 and 33 represent both selective positions. In this example, assembly 146b has a first mating surface 174 in the form of an ellipse (e.g., regular ellipse or superellipse), and valve 28b has a second mating surface 176 in the form of a similar ellipse. Second mating surface 176 encircles the valve's longitudinal centerline 156 and defines an oblong cross-sectional profile 178 that intersects and lies perpendicular to centerline 156. In some examples, as shown in FIG. 33, second mating surface 176 faces radially inward toward centerline 156. In other examples, where the valve's attachment end fits up inside a matching elliptical bore in a fluid exchanger, the valve's second mating elliptical surface faces radially outward away from centerline 156. With the illustrated example of valve 28b in either the first operating position or 180 degrees from that at the second operating position, in either position, elongate slit 172 lies in a direction that avoids interference between outer shell 24 and the valve's discharge end 150.

Figure 34:
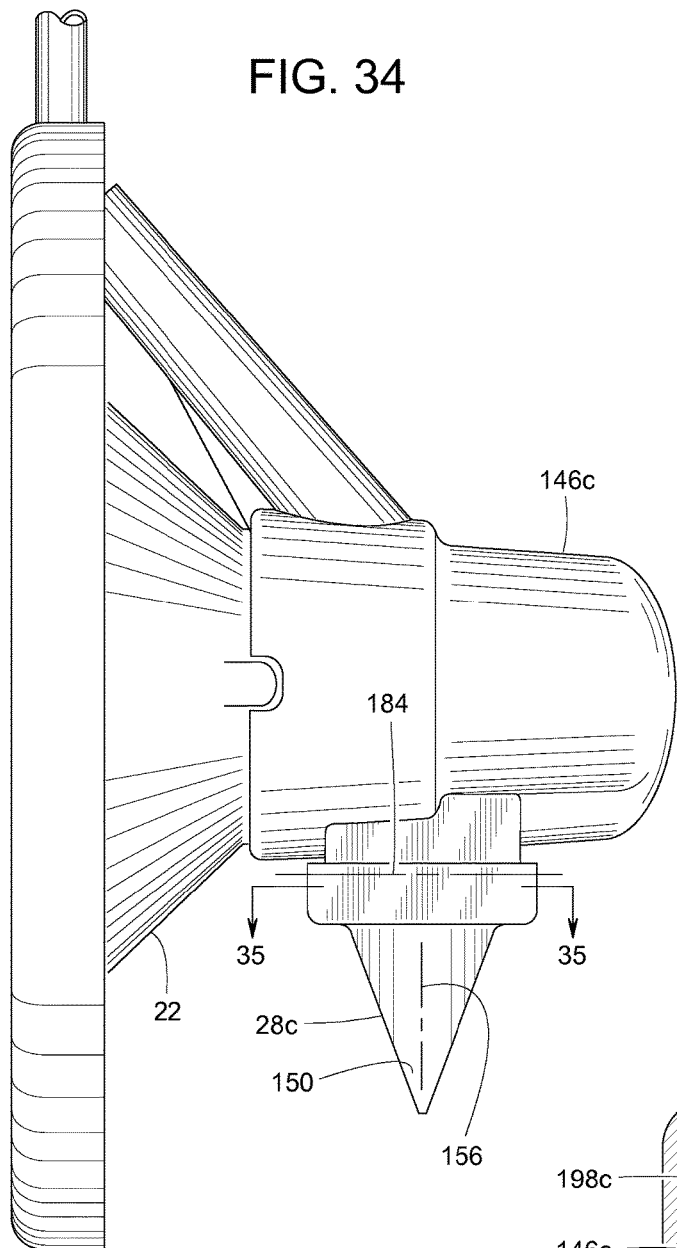
FIG. 34 is a side view similar to FIG. 24 but showing another example valve constructed in accordance with the teachings disclosed herein.
Figure 35:
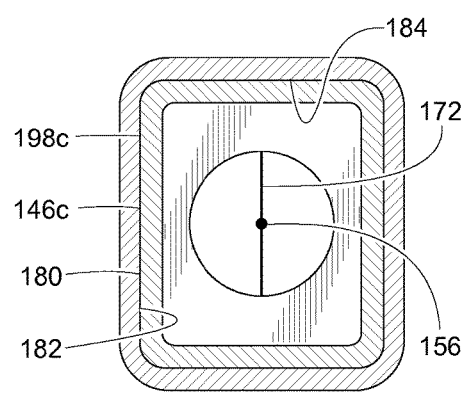
FIG. 35 is an enlarged cross-sectional view taken along line 35-35 of FIG. 34

In the example shown in FIGS. 34 and 35, a valve 28c can be positioned relative to an assembly 146c selectively to a first operating position (FIGS. 34 and 35) and to a second operating position. The second operating position is 180 degrees from the first one, so FIGS. 34 and 35 represent both selective positions. In this example, assembly 146c has a first mating surface 180 in the form of rectangle (e.g., regular rectangle or rounded rectangle), and valve 28c has a second mating surface 182 in the form of a similar rectangle. Second mating surface 182 encircles the valve's longitudinal centerline 156 and defines an oblong cross-sectional profile 184 that intersects and lies perpendicular to centerline 156. In some examples, as shown in FIG. 35, second mating surface 182 faces radially inward toward centerline 156. In other examples, where the valve's attachment end fits up inside a matching rectangular bore in a fluid exchanger, the valve's second mating rectangular surface faces radially outward away from centerline 156. With the illustrated example of valve 28c in either the first operating position or 180 degrees from that at the second operating position, in either position, elongate slit 172 lies in a direction that avoids interference between outer shell 24 and the valve's discharge end 150. In some examples (e.g., FIGS. 32-35 and/or designs similar to those), the second mating surface lies generally parallel to longitudinal centerline 156, which allows the valves to be readily installed and removed (e.g., slid on and off) yet provides mechanical resistance to rotation.

In the example shown in FIGS. 36-39, a valve 28d can be installed at any rotational position on an assembly 146d because an outer shell 24' and/or the combination of assembly 146d and valve 28d create clearance 186 or 188 between outer shell 24' and the valve's discharge end 150 regardless of the valve's rotational position on assembly 146d. In the illustrated example, a connecting interface 190 between assembly 146d and the valve's attachment end 148d is generally cylindrical. Connecting interface 190 being cylindrical provides valve 28d with infinite rotational mounting positions, including a first operating position (FIGS. 36 and 37) and a second operating position (FIGS. 38 and 39). Valve 28d can also be moved to a cleaning position by removing valve 28d from assembly 146d.

Figure 36:
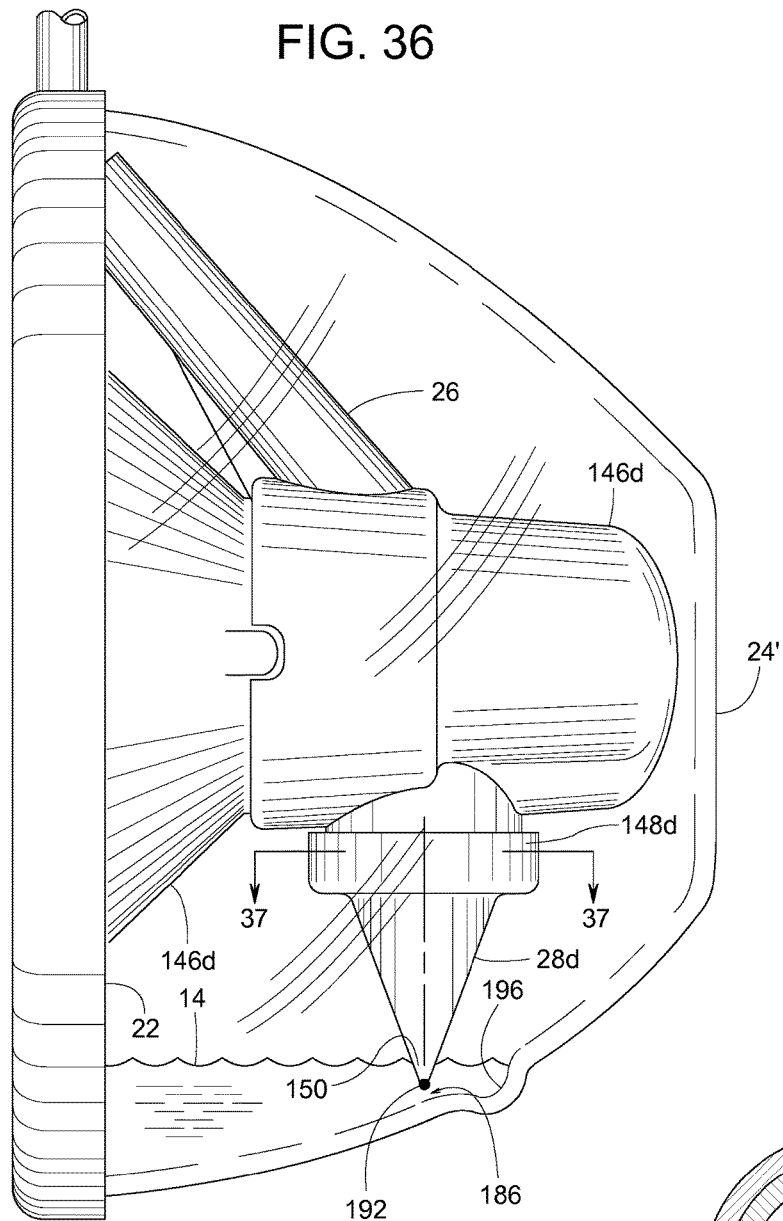
FIG. 36 is a side view similar to FIG. 23 but showing another example milk collection device constructed in accordance with the teachings disclosed herein.
Figure 37:
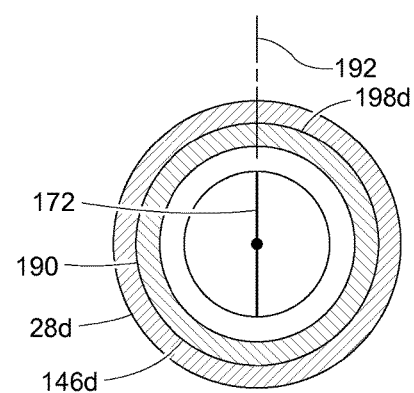
FIG. 37 is an enlarged cross-sectional view taken along line 37-37 of FIG. 36.

In the first operating position, shown in FIGS. 36 and 37, slit 172 extends along a first line 192. In the second operating position, shown in FIGS. 38 and 39, slit 172 extends along a second line 194, wherein lines 192 and 194 are substantially perpendicular to each other. In both the first and second operating positions, the valve's discharge end 150 is proximate yet spaced apart from outer shell 24', thus valve 28d is perfectly functional in either position. In some examples, the spaced apart clearance is due to outer shell 24' having a concavity 196 proximate the valve's discharge end 150. The valve's discharge end 150 protrudes farther into concavity 196 when valve 28d is in the second operating position (FIG. 38) than when valve 28d is in the first operating position (FIG. 36). In some examples, discharge end 150 does not even protrude into concavity 196 when valve 28d is in the first operating position.

For further clarification, the term, "suction tube" refers to any conduit having a tubular wall of sufficient thickness, stiffness, and/or strength to convey air at subatmospheric pressure. In some examples, suction tube 48 is more flexible than outer shell 24, breast receiver 22, and/or fluid exchanger 26. Such tube flexibility makes tube 48 easier to use and fit to fluid exchanger 26. The term, "coupled to" refers to two members being connected either directly without an intermediate connecting piece or being connected indirectly via an intermediate connecting piece between the two members. The term, "coupled to" encompasses permanent connections (e.g., bonded, welded, etc.), seamless connections (e.g., the two members are of a unitary piece), and separable connections. The term, "opening" of a fluid pathway refers to a cross-sectional area through which fluid is directed to flow in a direction generally perpendicular to the area as guided by the fluid pathway. The term, "radial gap" refers to clearance as measured in a direction perpendicular to longitudinal centerline 58. The terms, "negative pressure," "subatmospheric pressure," and "vacuum" all refer to a pressure that is less than atmospheric pressure. The term, "positive pressure," refers to a pressure that is greater than atmospheric pressure. Storage chamber 42 is not necessarily for long term storage but rather for collecting and temporarily storing milk 14 as the lactating woman is expressing milk. In some examples, milk collection device 12 includes a slot-and-key 144 alignment feature (FIG. 8) that establishes a certain desired rotational alignment (about longitudinal centerline 58) between fluid exchanger 26 and breast receiver 22.

In some examples, valve 28, 28a, 28b, 28c and/or 28d is softer than the assembly to which it is attached and thus enables the use of a radial press fit 198a, 198b, 198c and/or 198d between the valve and its respective assembly. The term, "rotationally interlocked" as it relates to two mating surfaces means that the surfaces include structural features that provide a mechanical obstruction that resists the relative rotation of the two surfaces about a specified centerline, wherein the mechanical obstruction is more than just friction alone. First and second mating surfaces being rotationally interlocked means that the surfaces include structural features that provide a mechanical obstruction that resists the relative rotation of the two surfaces; however, not the entirety of each surface needs to provide the obstruction. For instance, in some examples (e.g., FIGS. 29-31), a first area of a first surface provides a mechanical obstruction at one rotational position, and a second area of the first surface provides a mechanical obstruction at another rotational position. Moreover, the first and second areas of a given surface can be discrete separate areas that are spaced apart from each other. In some examples, a first surface comprises two spaced apart keys. In some examples, a second surface comprises two spaced apart slots. A surface extending or lying substantially parallel to the longitudinal centerline of the valve encompasses surfaces that have a slight draft angle (less than 8 degrees) for easing the part's removal from a mold cavity. The term, "proximate," as it pertains to "the discharge end being proximate yet spaced apart from the outer shell" means that the discharge end is within 2 centimeters of the nearest point on the outer shell. The term, "press fit" refers to the connection between two parts wherein dimensional interference between the two parts requires at least one of the parts being subjected to compressive or tensile strain upon being connected.

Although the invention is described with respect to a preferred embodiment, modifications thereto will be apparent to those of ordinary skill in the art. The scope of the invention, therefore, is to be determined by reference to the following claims:

The invention claimed is:
1. A breast pump system usable by a lactating woman for collecting milk, the breast pump system comprising:
   an outer shell;
   a breast receiver selectively coupled to the outer shell, the breast receiver comprising a breast guide and a nipple receptacle;
   the breast guide being adapted to engage a breast of the lactating woman;
   the nipple receptacle defining a nipple chamber adapted to receive a nipple of the breast;
   a storage chamber being defined between the outer shell and the breast receiver;
   a fluid exchanger coupled to the nipple receptacle such that the fluid exchanger and the breast receiver provides an assembly;
   a valve comprising an attachment end and a discharge end, the attachment end defining an attachment end central point centrally located at the attachment end, the discharge end defining a discharge end central point centrally located at the discharge end, the valve defining a longitudinal centerline extending from the attachment end central point to the discharge end central point, the valve being positioned selectively in first operating position and a cleaning position, the attachment end being connected to the assembly when the valve is in the first operating position, the attachment end being spaced apart from the assembly when the valve is in the cleaning position, the assembly being closer to the attachment end than to the discharge end when the valve is in the first operating position, the discharge end being proximate the outer shell when the breast receiver is coupled to the outer shell while the valve is in the first operating position;
   a charging chamber defined within at least one of the fluid exchanger and the valve, the charging chamber being connected in fluid communication with the nipple chamber, the valve connecting the charging chamber in at least momentary fluid communication with the storage chamber;
   a suction tube being connected in fluid communication with the charging chamber, the suction tube being more flexible than at least one of the outer shell, the breast receiver, and the fluid exchanger;
   a first mating surface on the assembly; and
   a second mating surface on the attachment end of the valve, the first mating surface and the second mating surface being rotationally interlocked at a first predetermined rotational position about the longitudinal centerline of the valve when the valve is in the first operating position, wherein the valve is further positioned selectively to a rotationally displaced position relative to the assembly, the attachment end of the valve being connected to the assembly when the valve is in the rotationally displaced position, the discharge end of the valve engaging the outer shell when the valve is in the rotationally displaced position while the breast receiver is coupled to the outer shell, and the discharge end of the valve being spaced apart from the outer shell when the valve is in the first operating position while the breast receiver is coupled to the outer shell.

2. The breast pump system of claim 1, wherein the second mating surface is a nonplanar axial surface at the attachment end of the valve and facing toward the assembly when the valve is in the first operating position.

3. The breast pump system of claim 1, wherein the second mating surface encircles the longitudinal centerline of the valve and defines a cross-sectional profile that intersects and lies perpendicular to the longitudinal centerline, the cross-sectional profile being oblong.

4. The breast pump system of claim 1, wherein the second mating surface encircles the longitudinal centerline of the valve and defines a cross-sectional profile that intersects and lies perpendicular to the longitudinal centerline, the cross-sectional profile being substantially elliptical.

5. The breast pump system of claim 1, wherein the second mating surface encircles the longitudinal centerline of the valve and defines a cross-sectional profile that intersects and lies perpendicular to the longitudinal centerline, the cross-sectional profile being substantially rectangular.

6. The breast pump system of claim 1, wherein the first mating surface and the second mating surface provide a first key-in-slot engagement that rotationally interlock at the first predetermined rotational position when the valve is in the first operating position.

7. The breast pump system of claim 1, wherein the valve is softer than the assembly and defines a slot that receives a key projection on the assembly when the valve is in the first operating position.

8. A breast pump system usable by a lactating woman for collecting milk, the breast pump system comprising:
   an outer shell;
   a breast receiver selectively coupled to the outer shell, the breast receiver comprising a breast guide and a nipple receptacle;
   the breast guide being adapted to engage a breast of the lactating woman;
   the nipple receptacle defining a nipple chamber adapted to receive a nipple of the breast;
   a storage chamber being defined between the outer shell and the breast receiver;
   a fluid exchanger coupled to the nipple receptacle such that the fluid exchanger and the breast receiver provides an assembly;
   a valve comprising an attachment end and a discharge end, the attachment end defining an attachment end central point centrally located at the attachment end, the discharge end defining a discharge end central point centrally located at the discharge end, the valve defining a longitudinal centerline extending from the attachment end central point to the discharge end central point, the valve being positioned selectively in first operating position and a cleaning position, the attachment end being connected to the assembly when the valve is in the first operating position, the attachment end being spaced apart from the assembly when the valve is in the cleaning position, the assembly being closer to the attachment end than to the discharge end when the valve is in the first operating position, the discharge end being proximate the outer shell when the breast receiver is coupled to the outer shell while the valve is in the first operating position;
   a charging chamber defined within at least one of the fluid exchanger and the valve, the charging chamber being connected in fluid communication with the nipple chamber, the valve connecting the charging chamber in at least momentary fluid communication with the storage chamber;

a suction tube being connected in fluid communication with the charging chamber, the suction tube being more flexible than at least one of the outer shell, the breast receiver, and the fluid exchanger;

a first mating surface on the assembly; and a second mating surface on the attachment end of the valve, the first mating surface and the second mating surface being rotationally interlocked at a first predetermined rotational position about the longitudinal centerline of the valve when the valve is in the first operating position;

wherein the valve is further positioned selectively to a second operating position, the attachment end being connected to the assembly when the valve is in the second operating position, the first mating surface and the second mating surface being rotationally interlocked at a second predetermined rotational position about the longitudinal centerline of the valve when the valve in the second operating position, and the first predetermined rotational position and the second predetermined rotational position are rotationally situated substantially 180 degrees apart from each other around the longitudinal centerline of the valve.

9. The breast pump system of claim 8, wherein the second mating surface is a nonplanar axial surface at the attachment end of the valve and facing toward the assembly when the valve is in the first operating position.

10. The breast pump system of claim 8, wherein the second mating surface encircles the longitudinal centerline of the valve and defines a cross-sectional profile that intersects and lies perpendicular to the longitudinal centerline, the cross-sectional profile being oblong.

11. The breast pump system of claim 8, wherein the second mating surface encircles the longitudinal centerline of the valve and defines a cross-sectional profile that intersects and lies perpendicular to the longitudinal centerline, the cross-sectional profile being substantially rectangular.

12. The breast pump system of claim 8, wherein the first mating surface and the second mating surface provide a first key-in-slot engagement that rotationally interlock at the first predetermined rotational position when the valve is in the first operating position.

13. The breast pump system of claim 8, wherein the valve is softer than the assembly and defines a slot that receives a key projection on the assembly when the valve is in the first operating position.

14. A breast pump system usable by a lactating woman for collecting milk, the breast pump system comprising:

an outer shell;

a breast receiver selectively coupled to the outer shell, the breast receiver comprising a breast guide and a nipple receptacle;

the breast guide being adapted to engage a breast of the lactating woman;

the nipple receptacle defining a nipple chamber adapted to receive a nipple of the breast;

a storage chamber being defined between the outer shell and the breast receiver;

a fluid exchanger coupled to the nipple receptacle such that the fluid exchanger and the breast receiver provides an assembly;

a valve comprising an attachment end and a discharge end, the attachment end defining an attachment end central point centrally located at the attachment end, the discharge end defining a discharge end central point centrally located at the discharge end, the valve defining a longitudinal centerline extending from the attachment end central point to the discharge end central point, the valve being positioned selectively in first operating position and a cleaning position, the attachment end being connected to the assembly when the valve is in the first operating position, the attachment end being spaced apart from the assembly when the valve is in the cleaning position, the assembly being closer to the attachment end than to the discharge end when the valve is in the first operating position, the discharge end being proximate the outer shell when the breast receiver is coupled to the outer shell while the valve is in the first operating position;

a charging chamber defined within at least one of the fluid exchanger and the valve, the charging chamber being connected in fluid communication with the nipple chamber, the valve connecting the charging chamber in at least momentary fluid communication with the storage chamber;

a suction tube being connected in fluid communication with the charging chamber, the suction tube being more flexible than at least one of the outer shell, the breast receiver, and the fluid exchanger;

a first mating surface on the assembly; and a second mating surface on the attachment end of the valve, the first mating surface and the second mating surface being rotationally interlocked at a first predetermined rotational position about the longitudinal centerline of the valve when the valve is in the first operating position, wherein the second mating surface is displaced out of perpendicularity with the longitudinal centerline of the valve.

15. The breast pump system of claim 14, wherein the second mating surface is a nonplanar axial surface at the attachment end of the valve and facing toward the assembly when the valve is in the first operating position.

16. The breast pump system of claim 14, wherein the second mating surface encircles the longitudinal centerline of the valve and defines a cross-sectional profile that intersects and lies perpendicular to the longitudinal centerline, the cross-sectional profile being oblong.

17. The breast pump system of claim 14, wherein the second mating surface encircles the longitudinal centerline of the valve and defines a cross-sectional profile that intersects and lies perpendicular to the longitudinal centerline, the cross-sectional profile being substantially elliptical.

18. The breast pump system of claim 14, wherein the second mating surface encircles the longitudinal centerline of the valve and defines a cross-sectional profile that intersects and lies perpendicular to the longitudinal centerline, the cross-sectional profile being substantially rectangular.

19. The breast pump system of claim 14, wherein the first mating surface and the second mating surface provide a first key-in-slot engagement that rotationally interlock at the first predetermined rotational position when the valve is in the first operating position.

20. The breast pump system of claim 14, wherein the valve is softer than the assembly and defines a slot that receives a key projection on the assembly when the valve is in the first operating position.

* * * * *